(12) United States Patent
Furuta et al.

(10) Patent No.: US 10,600,574 B2
(45) Date of Patent: *Mar. 24, 2020

(54) ORGANIC COMPOUND, CRYSTAL DIELECTRIC LAYER AND CAPACITOR

(71) Applicant: Capacitor Sciences Incorporated, Menlo Park, CA (US)

(72) Inventors: Paul Furuta, Sunnyvale, CA (US); Pavel Ivan Lazarev, Menlo Park, CA (US)

(73) Assignee: CAPACITOR SCIENCES INCORPORATED, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/036,817

(22) Filed: Jul. 16, 2018

(65) Prior Publication Data

US 2019/0139706 A1    May 9, 2019

Related U.S. Application Data

(63) Continuation-in-part of application No. 14/919,337, filed on Oct. 21, 2015, now Pat. No. 10,026,553.

(51) Int. Cl.
  *H01G 4/14* (2006.01)
  *C07D 471/22* (2006.01)
  *C07D 471/06* (2006.01)

(52) U.S. Cl.
  CPC ............ *H01G 4/14* (2013.01); *C07D 471/06* (2013.01); *C07D 471/22* (2013.01)

(58) Field of Classification Search
  CPC .................................................. H01G 4/14
  USPC ........................................................ 546/27
  See application file for complete search history.

(56) References Cited

U.S. PATENT DOCUMENTS

| | | | |
|---|---|---|---|
| 4,549,034 A | 10/1985 | Sato et al. | |
| 7,342,755 B1 | 3/2008 | Horvat et al. | |
| 7,678,907 B2 | 3/2010 | Koenemann et al. | |
| 7,990,679 B2 | 8/2011 | Ehrenberg et al. | |
| 9,899,150 B2 | 2/2018 | Lazarev | |
| 9,916,931 B2 | 3/2018 | Lazarev | |
| 9,978,517 B2 | 5/2018 | Lazarev et al. | |
| 10,153,087 B2 | 12/2018 | Lazarev et al. | |
| 2007/0003781 A1 | 1/2007 | Rochemont | |
| 2008/0002329 A1 | 1/2008 | Pohm et al. | |
| 2008/0255357 A1 | 10/2008 | Pschirer et al. | |
| 2010/0011656 A1 | 1/2010 | Gessner et al. | |
| 2010/0172066 A1 | 7/2010 | Baer et al. | |
| 2010/0178728 A1 | 7/2010 | Zheng et al. | |
| 2010/0193777 A1 | 8/2010 | Takahashi et al. | |
| 2011/0079733 A1 | 4/2011 | Langhals et al. | |
| 2011/0149393 A1 | 6/2011 | Nokel et al. | |
| 2012/0122274 A1 | 5/2012 | Lazarev | |
| 2015/0235769 A1 | 8/2015 | Carver et al. | |
| 2017/0133167 A1 | 5/2017 | Keller et al. | |
| 2018/0033554 A1 | 2/2018 | Li et al. | |
| 2018/0122143 A1 | 5/2018 | Ellwood | |
| 2018/0158616 A1 | 6/2018 | Lazarev et al. | |

FOREIGN PATENT DOCUMENTS

| | | |
|---|---|---|
| CN | 103258656 B | 8/2015 |
| DE | 4316378 A1 | 11/1994 |
| EP | 2108673 A1 | 10/2009 |
| EP | 1990682 B1 | 1/2015 |
| JP | 2001093778 A | 4/2001 |
| WO | 2008085942 A2 | 7/2008 |
| WO | 2009144205 A1 | 12/2009 |
| WO | 2011137137 A1 | 11/2011 |
| WO | 2012142460 A1 | 10/2012 |
| WO | 2013085467 A1 | 6/2013 |

OTHER PUBLICATIONS

Extended European Search Report dated Aug. 8, 2018 for European Patent Application No. 16756391.5.
Extended European Search Report dated Sep. 24, 2018 for European Patent Application No. 15856609.1.
Extended European Search Report dated Sep. 26, 2018 for European Patent Application No. 16797411.2.
Final Office Action for U.S. Appl. No. 15/449,587, dated Oct. 10, 2018.
M. Jurow et al, "Porphyrins as molectular electronic components of functional devices", Coordination Chemistry Reviews, Elsevier Science, Amsterdam NL, vol. 254, No. 19-20, Oct. 1, 2010, pp. 2297-2310.

(Continued)

*Primary Examiner* — Taofiq A Solola
(74) *Attorney, Agent, or Firm* — BCF LLP

(57) ABSTRACT

The present disclosure provides an organic compound characterized by electronic polarizability and having a following general structural formula:

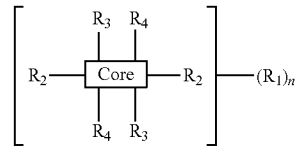

where Core is an aromatic polycyclic conjugated molecule, $R_1$ is an insulating group, n is 1, 2, 3, 4, 5, 6, 7 or 8, $R_2$ is substitute located in apex positions, R3 and R4 are located in side (lateral) positions and, the core has flat anisometric form and $R_2$ are selected from hydrogen and nucleophilic groups (donors) and $R_3$ and $R_4$ are independently selected from hydrogen and electrophilic groups (acceptors) or vice versa $R_3$ and $R_4$ are independently selected from hydrogen and nucleophilic groups (donors) and $R_2$ are selected from hydrogen and electrophilic groups (acceptors).

8 Claims, 1 Drawing Sheet

(56) References Cited

OTHER PUBLICATIONS

Non-Final Office Action for U.S. Appl. No. 15/782,752, dated Sep. 21, 2018.
Non-Final Office Action for U.S. Appl. No. 15/430,307, dated Jul. 16, 2018.
Non-Final Office Action for U.S. Appl. No. 15/801,240, dated Oct. 19, 2018.
Non-Final/Final Office Action for U.S. Appl. No. 15/430,391, dated Jul. 20, 2018.
Notice of Allowance for U.S. Appl. No. 15/163,595, dated Jul. 30, 2018.
Final Office Action for U.S. Appl. No. 15/043,247, dated Oct. 24, 2018.
Final Office Action for U.S. Appl. No. 15/710,587, dated Nov. 6, 2018.
Non-Final Office Action for U.S. Appl. No. 15/043,247, dated Feb. 19, 2019.
Non-Final Office Action for U.S. Appl. No. 15/870,504, dated Feb. 27, 2019.
Notice of Allowance for U.S. Appl. No. 15/043,315, dated Feb. 21, 2019.
Notice of Allowance for U.S. Appl. No. 15/043,315, dated Jan. 15, 2019.
Notice of Allowance for U.S. Appl. No. 15/449,524, dated Feb. 21, 2019.
Notice of Allowance for U.S. Appl. No. 15/710,587, dated Jan. 24, 2019.
Notice of Allowance for U.S. Appl. No. 15/782,752, dated Feb. 25, 2019.
Notice of Allowance for U.S. Appl. No. 15/801,240, dated Feb. 11, 2019.
Office Action dated Jan. 29, 2019 for Japanese Patent Application No. 2017-512654.
Supplementary Notice of Allowance for U.S. Appl. No. 14/752,600, dated Dec. 4, 2017.
Taiwanese Office Action for 886103 Application No. 106142206, dated Jul. 5, 2018.
English translation of the abstract of DE 4316378.
Supplementary European Search Report issued in corresponding application EP 1685815.7 dated May 22, 2019.

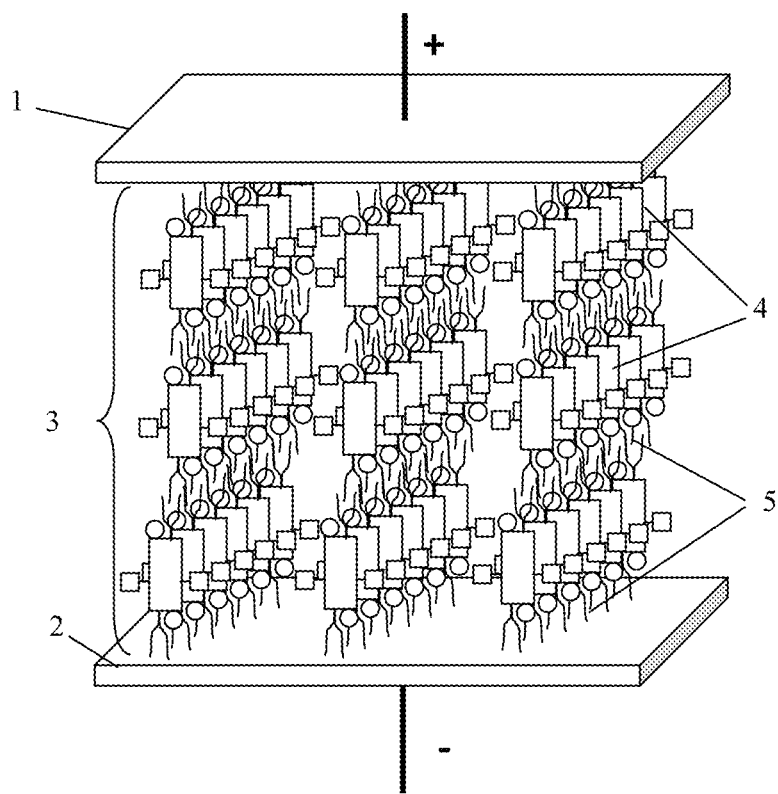

ORGANIC COMPOUND, CRYSTAL DIELECTRIC LAYER AND CAPACITOR

CLAIM OF PRIORITY

This application is a continuation-in-parts of U.S. patent application Ser. No. 14/919,337, filed Oct. 21, 2015, the entire contents of which are incorporated herein by reference.

BACKGROUND

A capacitor is a passive electronic component that is used to store energy in the form of an electrostatic field and comprises a pair of electrodes separated by a dielectric layer. Each of the electrodes has an area A and are separated from each other by a distance d. When a potential difference exists between two electrodes, an electric field is present in the dielectric layer. This field stores energy and an ideal capacitor is characterized by a single constant value of capacitance which is the ratio of the electric charge on each electrode to the potential difference between them. Charge may be considered to be distributed uniformly over the area A of each electrode, and a surface charge density $\sigma$ for each electrode can be expressed as $\pm\sigma=\pm Q/A$. As the width of the electrodes is much greater than the separation (distance) d, an electrical field near the center of the capacitor will be uniform with the magnitude $E=\rho/\varepsilon$. Voltage is defined as a line integral of the electric field between electrodes. An ideal capacitor is characterized by a constant capacitance C, defined by the formula (1)

$$C=Q/V, \quad (1)$$

which shows that capacitance increases with area and decreases with distance. For high voltage applications much larger capacitors have to be used.

One of important characteristic of a dielectric material is its breakdown voltage $V_{bd}$. There are a number of factors that can dramatically reduce the breakdown voltage that is a breakdown of dielectric layer along electric field lines will take place. Geometry of the conductive electrodes is important for these applications. In particular, sharp edges or points hugely increase the electric field strength locally and can lead to a local breakdown. Once a local breakdown starts at any point, the breakdown will quickly "trace" through the dielectric layer till it reaches the opposite electrode and causes a short circuit.

Breakdown of the dielectric layer usually occurs as follows. Intensity of an electric field becomes high enough to "pull" electrons from atoms of the dielectric material and make them conduct an electric current from one electrode to another. Presence of impurities in the dielectric or imperfections of the crystal structure can result in an avalanche breakdown as observed in semiconductor devices.

A characteristic electric field known as the breakdown strength $E_{bd}$, is the electric field intensity at which the dielectric layer in a capacitor becomes conductive. The breakdown voltage is related to the breakdown strength by the product of dielectric strength and separation between the electrodes, $$V_{bd}=E_{bd}d \quad (2)$$

Another of important characteristic of a dielectric material is its dielectric permittivity $\varepsilon$. Different types of dielectric materials are used for capacitors and include ceramics, polymer film, paper, and electrolytic capacitors of different kinds. The most widely used polymer film materials are polypropylene and polyester. Increase of dielectric permittivity allows increasing of volumetric energy density which makes it an important technical task. The dielectric permittivity c for a material is often expressed as the product of a dimensionless dielectric constant $\kappa$ and the permittivity of free space $\varepsilon_0$ ($8.85 \times 10^{-12}$ Farads/meter). Therefore the capacitance is largest in devices made of materials of high permittivity.

The maximal volumetric energy density stored in the capacitor is proportional to $\sim \varepsilon \cdot E^2_{bd}$. Thus, in order to increase the stored energy of the capacitor it is necessary to increase dielectric permittivity $\varepsilon$ (or dielectric constant $\kappa$) and breakdown strength $E_{bd}$ of the dielectric material.

An ultra-high dielectric constant composite of polyaniline, PANI-DBSA/PAA, was synthesized using in situ polymerization of aniline in an aqueous dispersion of polyacrylic acid (PAA) in the presence of dodecylbenzene sulfonate (DBSA) (see, Chao-Hsien Hoa et al., "High dielectric constant polyaniline/poly(acrylic acid) composites prepared by in situ polymerization", Synthetic Metals 158 (2008), pp. 630-637). The water-soluble PAA served as a polymeric stabilizer, protecting the PANI particles from macroscopic aggregation. A very high dielectric constant of ca. $2.0*10^5$ (at 1 kHz) was obtained for the composite containing 30% PANI by weight. Influence of the PANI content on the morphological, dielectric and electrical properties of the composites was investigated. Frequency dependence of dielectric permittivity, dielectric loss, loss tangent and electric modulus were analyzed in the frequency range from 0.5 kHz to 10 MHz. SEM micrograph revealed that composites with high PANI content (i.e., 20 wt. %) consisted of numerous nano-scale PANI particles that were evenly distributed within the PAA matrix. High dielectric constants were attributed to the sum of the small capacitors of the PANI particles. The drawback of this material is a possible occurrence of percolation and formation of at least one continuous electrically conductive channel under electric field with probability of such an event increasing with an increase of the electric field. When at least one continuous electrically conductive channel (track) through the neighboring conducting PANI particles is formed between electrodes of the capacitor, it decreases a breakdown voltage of such capacitor.

Colloidal polyaniline particles stabilized with a water-soluble polymer, poly(N-vinylpyrrolidone) [poly(1-vinylpyrrolidin-2-one)], have been prepared by dispersion polymerization. The average particle size, 241±50 nm, have been determined by dynamic light scattering (see, Jaroslav Stejskal and Irina Sapurina, "Polyaniline: Thin Films and Colloidal Dispersions (IUPAC Technical Report)", Pure and Applied Chemistry, Vol. 77, No. 5, pp. 815-826 (2005).

Single crystals of doped aniline oligomers are produced via a simple solution-based self-assembly method (see, Yue Wang, et. al., "Morphological and Dimensional Control via Hierarchical Assembly of Doped Oligoaniline Single Crystals", J. Am. Chem. Soc. 2012, 134, pp. 9251-9262). Detailed mechanistic studies reveal that crystals of different morphologies and dimensions can be produced by a "bottom-up" hierarchical assembly where structures such as one-dimensional (1-D) nanofibers can be aggregated into higher order architectures. A large variety of crystalline nanostructures, including 1-D nanofibers and nanowires, 2-D nanoribbons and nanosheets, 3-D nanoplates, stacked sheets, nanoflowers, porous networks, hollow spheres, and twisted coils, can be obtained by controlling the nucleation of the crystals and the non-covalent interactions between the doped oligomers. These nanoscale crystals exhibit enhanced conductivity compared to their bulk counterparts as well as interesting structure-property relationships such as shape-dependent crystallinity. Furthermore, the morphology and dimension of these structures can be largely rationalized and predicted by monitoring molecule-solvent interactions via absorption studies. Using doped tetra-aniline as a model system, the results and strategies presented in this article provide insight into the general scheme of shape and size control for organic materials.

Thus, materials with high dielectric permittivity which are based on composite materials and containing polarized particles (such as PANI particles) may demonstrate a percolation phenomenon. The formed polycrystalline structure of layers has multiple tangling chemical bonds on borders between crystallites. When the used material with high dielectric permittivity possesses polycrystalline structure, a percolation may occur along the borders of crystal grains.

Hyper-electronic polarization of organic compounds is described in greater detail in Roger D. Hartman and Herbert A. Pohl, "Hyper-electronic Polarization in Macromolecular Solids", Journal of Polymer Science: Part A-1 Vol. 6, pp. 1135-1152 (1968). Hyper-electronic polarization may be viewed as the electrical polarization external fields due to the pliant interaction with the charge pairs of excitons, in which the charges are molecularly separated and range over molecularly limited domains. In this article four polyacene quinone radical polymers were investigated. These polymers at 100 Hz had dielectric constants of 1800-2400, decreasing to about 58-100 at 100,000 Hz. An essential drawback of the described method of production of material is use of a high pressure (up to 20 kbars) for forming the samples intended for measurement of dielectric constants.

Capacitors as energy storage device have well-known advantages versus electrochemical energy storage, e.g. a battery. Compared to batteries, capacitors are able to store energy with very high power density, i.e., very high charge/recharge rates, have long shelf life with little degradation, and can be charged and discharged (cycled) hundreds of thousands or millions of times. However, conventional capacitors often do not store energy in a sufficiently small volume or weight as compared to the case of a battery, or at low energy storage cost, which makes capacitors impractical for some applications, for example electric vehicles. Accordingly, it may be an advance in energy storage technology to provide capacitors of higher volumetric and mass energy storage density and lower cost.

SUMMARY

The present disclosure provides an organic compound characterized by electronic polarizability and having a following general structural formula:

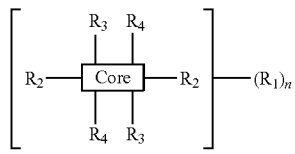

where Core is an aromatic polycyclic conjugated fragment, $R_1$ are insulating groups which in some instances provide solubility of the organic compound in an organic solvent, n is 1, 2, 3, 4, 5, 6, 7 or 8, $R_2$ are substituents located in apex positions, $R_3$ and $R_4$ are located in side (lateral) positions and, the core has flat anisometric form and the $R_2$ are selected from hydrogen and nucleophilic groups (donors) and $R_3$ and $R_4$ are independently selected from hydrogen and electrophilic groups (acceptors) or vice versa $R_3$ and $R_4$ are independently selected from hydrogen and nucleophilic groups (donors) and $R_2$ are selected from hydrogen and electrophilic groups (acceptors).

In an aspect, the present disclosure provides a dielectric layer comprising the disclosed organic compound. Further still, in some embodiments the dielectric layer comprises a mixture of embodiments of the disclosed organic compound. For example, in some embodiments the dielectric layer is comprised of regioisomers of the disclosed organic compound. In some embodiments, the dielectric layer is crystalline.

In another aspect, the present disclosure provides a capacitor comprising a first electrode, a second electrode, and a crystal dielectric layer disposed between said first and second electrodes, wherein said electrodes are more or less flat and planar and positioned more or less parallel to each other, and wherein said crystal dielectric layer comprises the disclosed organic compound. Said crystal dielectric layer comprises supramolecules formed with the aromatic polycyclic conjugated cores, and isotropic insulating sublayers formed with the substitutes served as the isolating groups Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWING

FIG. 1 schematically shows a capacitor according to an aspect of the present disclosure.

DETAILED DESCRIPTION

While various implementations of aspects of the present disclosure have been shown and described herein, it will be obvious to those skilled in the art that such implementations are provided by way of example only. Numerous variations, changes, and substitutions may occur to those skilled in the art without departing from the aspects of the present disclosure. It should be understood that various alternatives to the implementations described herein may be employed.

The present disclosure provides an organic compound. Existence of the aromatic polycyclic conjugated fragment promotes electronic polarizability of these organic compounds. Under the influence of an external electric field electrons are displaced from positive to negative field. In some embodiments, existence of at least one electrophilic group (acceptor), or at least one nucleophilic group (donor), or at least one of each on the aromatic polycyclic conjugated core can promote polarizability under influence of an external electric field.

The $R_1$ groups can be connected via the $R_2$ groups, alternatively they can be directly connected to the Core. In some implementations, the $R_1$ groups serve as insolating groups and are attached to the aromatic polycyclic conjugated core in apex positions. In some implementations, the $R_1$ groups serve as insolating groups and are attached to the aromatic polycyclic conjugated core in side positions. In some implementations, the $R_1$ groups serve as insolating groups and are attached to the aromatic polycyclic conjugated core on apex and/or side positions.

In some implementations, the $R_1$ groups are independently selected from the group consisting of hetero-alkyl $C_1$-$C_{18}$, hetero-alkenyl $C_1$-$C_{18}$, hetero-alkynyl $C_1$-$C_{18}$, hetero-aryl $C_1$-$C_{18}$, unsubstituted $C_1$-$C_{18}$ alkyl, substituted $C_1$-$C_{18}$ alkyl, unsubstituted $C_2$-$C_{18}$ alkenyl, substituted $C_2$-$C_{18}$ alkenyl, unsubstituted $C_2$-$C_{18}$ alkynyl, substituted $C_2$-$C_{18}$ alkynyl, unsubstituted $C_4$-$C_{18}$ aryl, substituted $C_4$-$C_{18}$ aryl, fluorinated alkyl, chlorinated alkyl, complex alkyl, branched alkyl, complex fluorinated alkyl, branched fluorinated alkyl, complex chlorinated alkyl, branched chlorinated alkyl, and any combination thereof, and wherein hetero atoms are selected from N, O, S, Si, and P.

In another embodiment of the present invention, the aromatic polycyclic conjugated Core in the above general structural formula comprises rylene fragments. In still another embodiment of the present invention, the rylene fragments are selected from structures 1-7 as given in Table 1.

TABLE 1

Examples of the polycyclic organic compound comprising rylene fragments

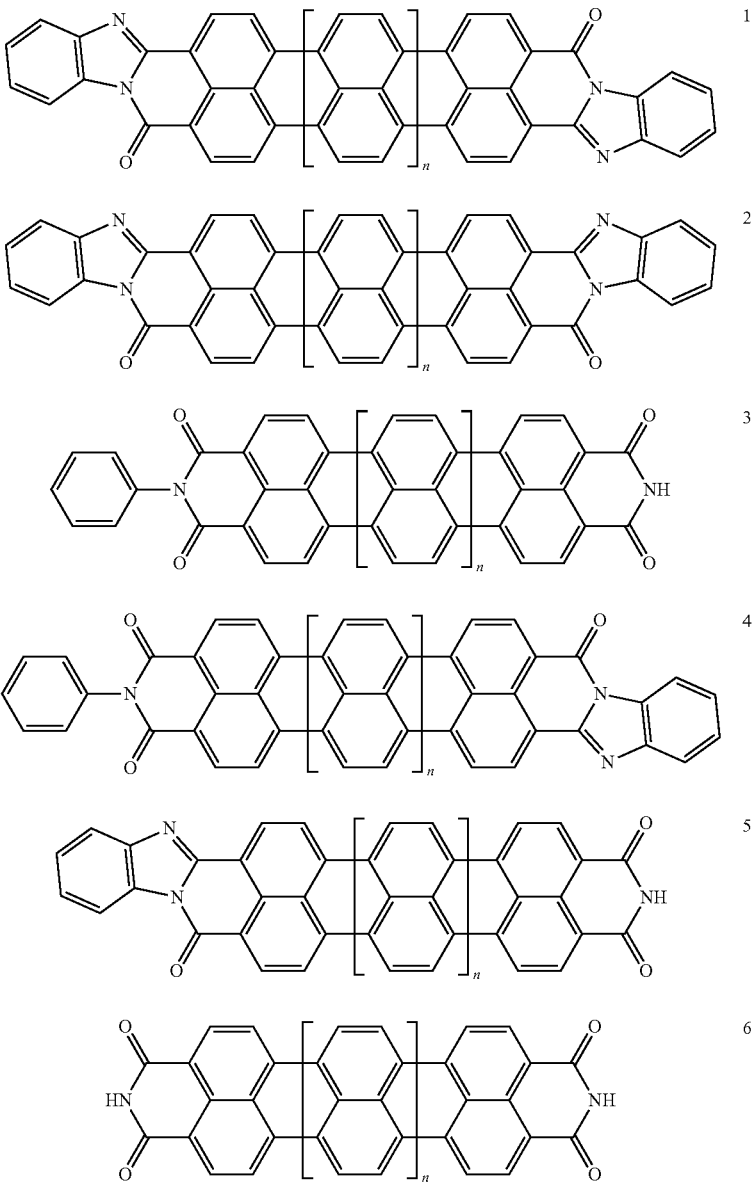

TABLE 1-continued

Examples of the polycyclic organic compound comprising rylene fragments

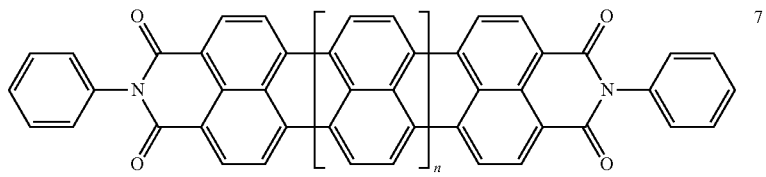

7 wherein n is an integer ranging from 0 to 3.

In one embodiment the organic compound, the Core and insulating group combination, e.g. [Core]-($R_1$) may have a base structure:

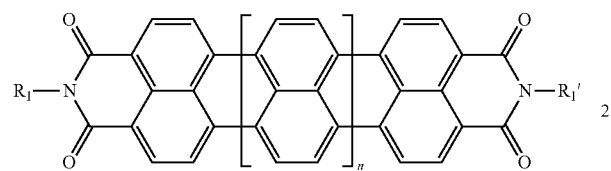

wherein n is an integer ranging from 0-3, and wherein $R_1$ and $R_1'$ are independently selected from the group consisting of hetero-alkyl $C_1$-$C_{18}$, hetero-alkenyl $C_1$-$C_{18}$, hetero-alkynyl $C_1$-$C_{18}$, hetero-aryl $C_1$-$C_{18}$, unsubstituted $C_1$-$C_{18}$ alkyl, substituted $C_1$-$C_{18}$ alkyl, unsubstituted $C_2$-$C_{18}$ alkenyl, substituted $C_2$-$C_{18}$ alkenyl, unsubstituted $C_2$-$C_{18}$ alkynyl, substituted $C_2$-$C_{18}$ alkynyl, unsubstituted $C_4$-$C_{18}$ aryl, substituted $C_4$-$C_{18}$ aryl, fluorinated alkyl, chlorinated alkyl, complex alkyl, branched alkyl, complex fluorinated alkyl, branched fluorinated alkyl, complex chlorinated alkyl, branched chlorinated alkyl, and any combination thereof; and wherein hetero atoms are selected from N, O, S, Si, and P.

In some embodiments, selection of nucleophiles is made for increasing overall electron density of the organic compound. Further, position or placement of nucleophile groups is made based on enhancing non-linear polarizability of the organic compound. Still further, in some embodiments nucleophiles and/or electrophiles are positioned such that the organic compound has a centrosymmetric structure. In some embodiments at least one electrophile is present to enhance the non-linear polarizability of the organic compound. In some embodiments, the Core is centrosymmetric. In still some embodiments, the Core is non-centrosymmetric.

In another implementation of the organic compound, the aromatic polycyclic conjugated Core in the above general structural formula comprises an electro-conductive oligomer including a phenylene oligomer and a polyacene quinine radical oligomer. In still another embodiment of the present invention, the electro-conductive oligomer is selected from the structures 8 to 16 as given in Table 2 wherein I=2, 3, 4, 5, 6, 7, 8, 9, 10, 11 or 12, Z is =O, =S or =$NR_1R_1'$, and $R_1$ and $R_1'$ are selected from the group consisting of unsubstituted or substituted $C_1$-$C_{18}$alkyl, unsubstituted or substituted $C_2$-$C_{18}$alkenyl, unsubstituted or substituted $C_2$-$C_{18}$alkynyl, and unsubstituted or substituted $C_4$-$C_{18}$aryl.

TABLE 2

Examples of the polycyclic organic compound comprising electro-conductive oligomer

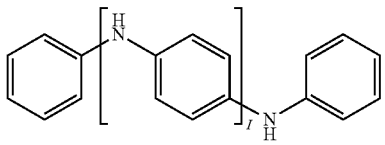

8

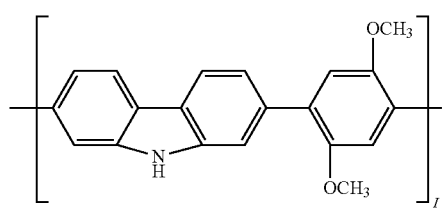

9

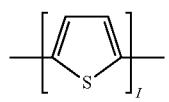

10

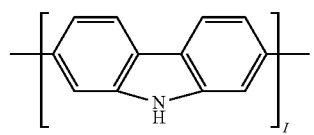

11

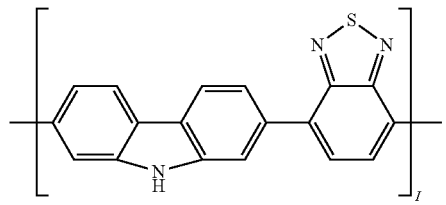

12

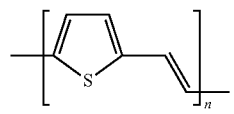

13

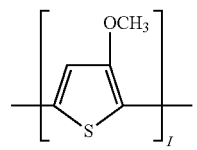

14

TABLE 2-continued

Examples of the polycyclic organic compound comprising electro-conductive oligomer

15

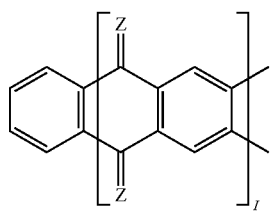

16

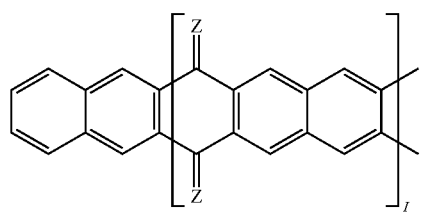

In yet another implementation, the aforementioned electrophilic groups (acceptors) in the above general structural formula are selected from —$NO_2$, —$NH_3^+$ and —$NR_3^+$ and —$NRR'R'^+$ (counterion $Cl^-$ or $Br^-$), —CHO (aldehyde), —CRO (keto group), —$SO_3H$ (sulfonic acids), —$SO_3R$ (sulfonates), —$SO_2NH_2$, —$SO_2NRR'$, —COOH, —COOR, —COCl, —$CONH_2$ (amides, from carboxylic acid side), —CONRR', —$CF_3$, —$CCl_3$, —CN, wherein R and R' and R" are radicals independently selected from the list comprising alkyl (methyl, ethyl, isopropyl, tert-butyl, neopentyl, cyclohexyl etc.), allyl (—$CH_2$—CH=$CH_2$), benzyl (—$CH_2C_6H_5$) groups, phenyl (+substituted phenyl) and other aryl (aromatic) groups.

In still another implementation, the aforementioned nucleophilic groups (donors) in the above general structural formula are selected from —$O^-$ (phenoxides, like —ONa or —OK), —$NH_2$, —NHR, $NR_2$, —OH, OR (ethers), —NHCOR (amides, from amine side), —OCOR (esters, from alcohol side), alkyls, —$C_6H_5$, vinyls, wherein R is radical selected from the list comprising alkyl (methyl, ethyl, isopropyl, tert-butyl, neopentyl, cyclohexyl etc.), allyl (—$CH_2$—CH=$CH_2$), benzyl (—$CH_2C_6H_5$) groups, phenyl (+substituted phenyl) and other aryl (aromatic) groups. In one implementation, the organic solvent is selected from benzene, toluene, xylenes, acetone, acetic acid, methylethylketone, hydrocarbons, chloroform, carbontetrachloride, methylenechloride, dichlorethane, chlorobenzene, alcohols, nitromethan, acetonitrile, dimethylforamide, 1,4-dioxane, tetrahydrofuran (THF), methylcyclohexane (MCH), and any combination thereof. In another implementation, the insulating groups which in some instances provide solubility of the organic compound are independently selected from alkyl, aryl, substituted alkyl, substituted aryl, fluorinated alkyl, chlorinated alkyl, branched and complex alkyl, branched and complex fluorinated alkyl, branched and complex chlorinated alkyl groups, and any combination thereof, and wherein the alkyl group is selected from methyl, ethyl, propyl, butyl, I-butyl and t-butyl groups, and the aryl group is selected from phenyl, benzyl and naphthyl groups.

In yet another implementation, the aromatic polycyclic conjugated Core in the above general structural formula comprises rylene fragment, the amino groups (—$NH_2$) are used as donors, nitro groups are used as acceptors and said organic compound formulas are selected from structures 17 to 22 as shown in Table 3.

TABLE 3

Examples of the organic compound

17

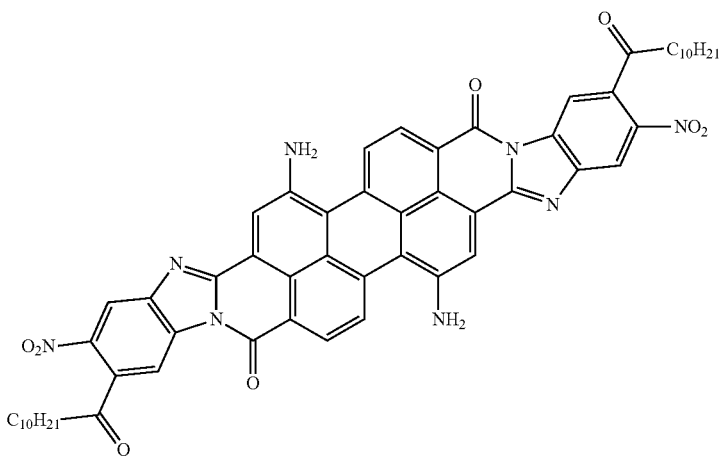

TABLE 3-continued
Examples of the organic compound
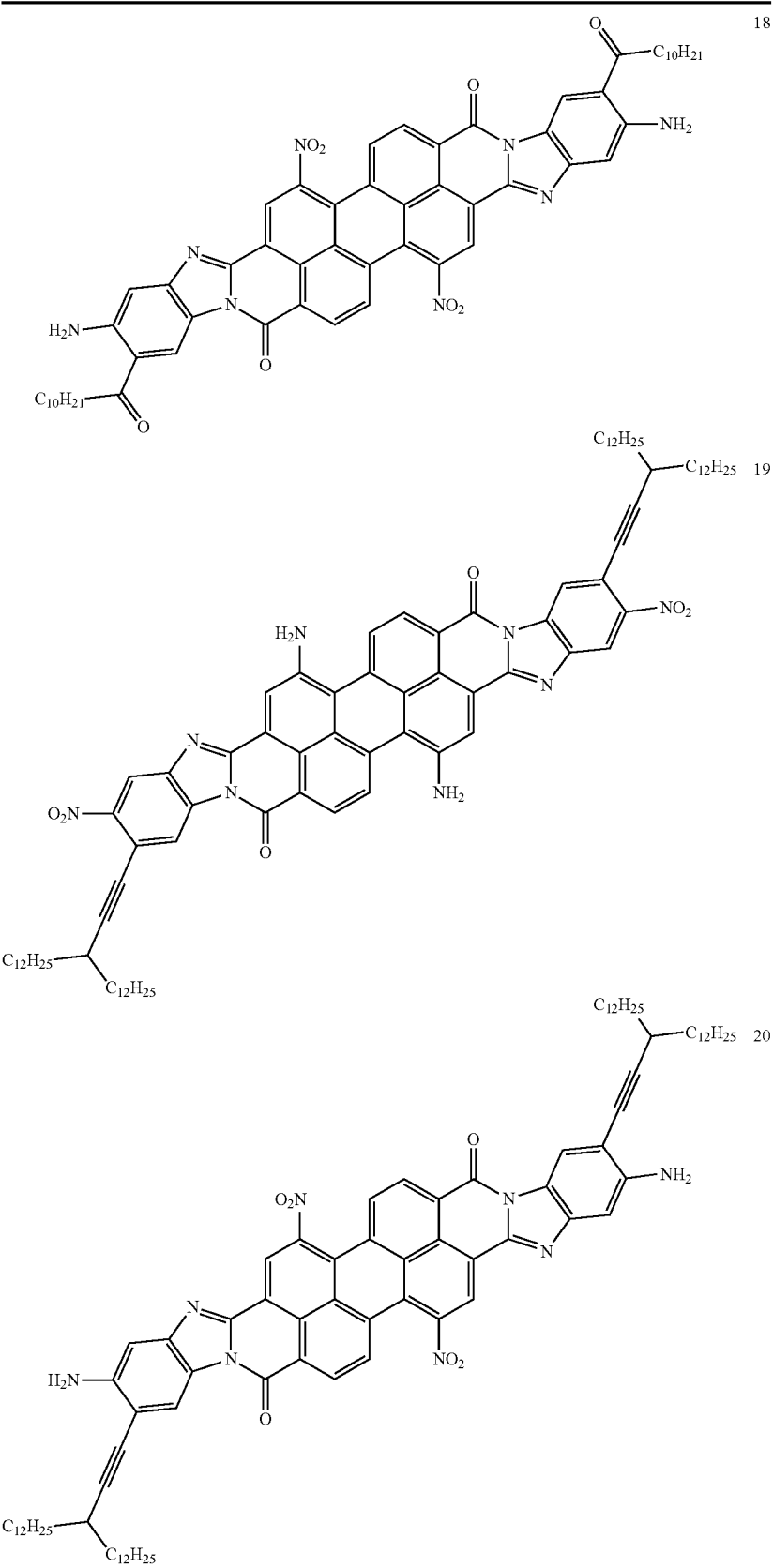

TABLE 3-continued

Examples of the organic compound

[Structure 21: Perylene diimide core with two NO₂ substituents on the core, and N-substituents of -CH(C₁₂H₂₅)-NH₂ on both imide nitrogens]

[Structure 22: Perylene diimide core with two NH₂ substituents on the core, and N-substituents of -CH(C₁₂H₂₅)-NO₂ on both imide nitrogens]

In yet another implementation, the aromatic polycyclic conjugated Core in the above general structural formula comprises rylene fragment and selected from structures 23-25 as shown in Table 4, where other ring position of $R_1$ and $R_2$ are possible so that regio-isomers are possible.

TABLE 4

Examples of the organic compound

[Structure 23: Perylene diimide with N-aryl substituents bearing $R_1$ and $R_2$ groups; core positions labeled $R_3$ and $R_4$]

[Structure 24: Extended rylene-based polycyclic structure with fused phenanthridine-type rings; positions labeled $R_1$, $R_2$, $R_3$, $R_4$]

TABLE 4-continued
Examples of the organic compound
25
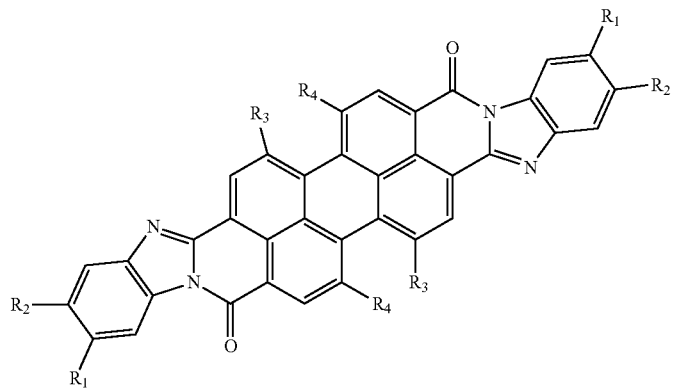
In still another embodiment of the present invention, the aromatic polycyclic conjugated Core in the above general structural formula comprises rylene fragment and has a structure selected from structures 26-32 as shown in Table 5.
TABLE 5
Examples of the organic compound
26
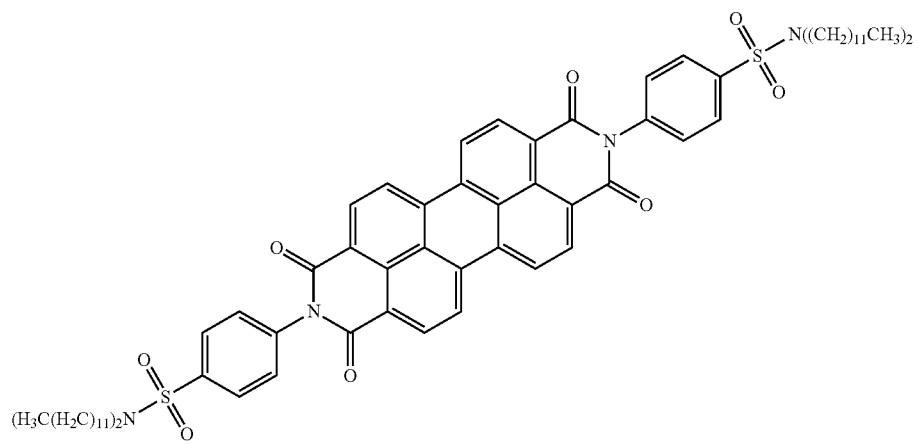
27
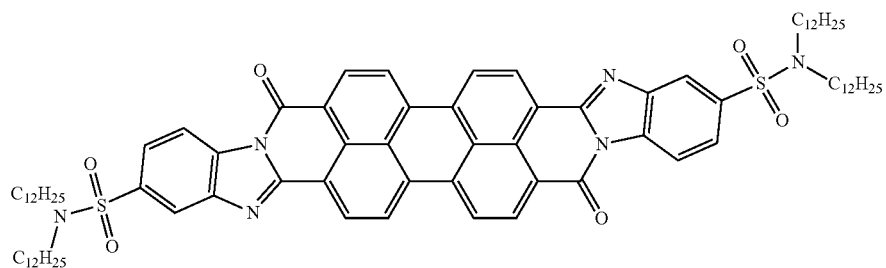

TABLE 5-continued
Examples of the organic compound
28
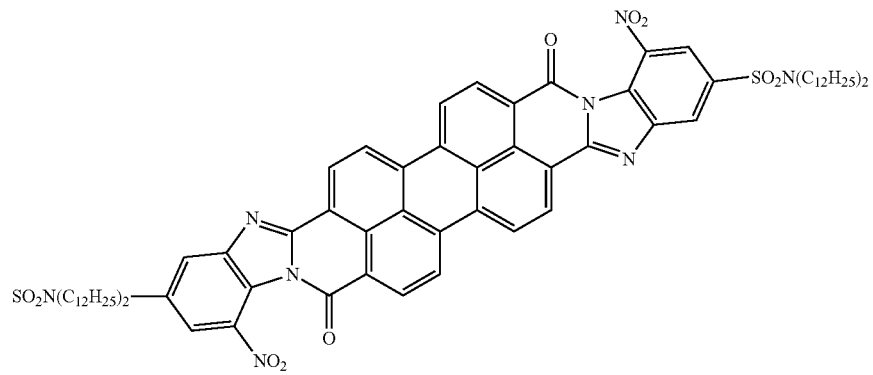
29
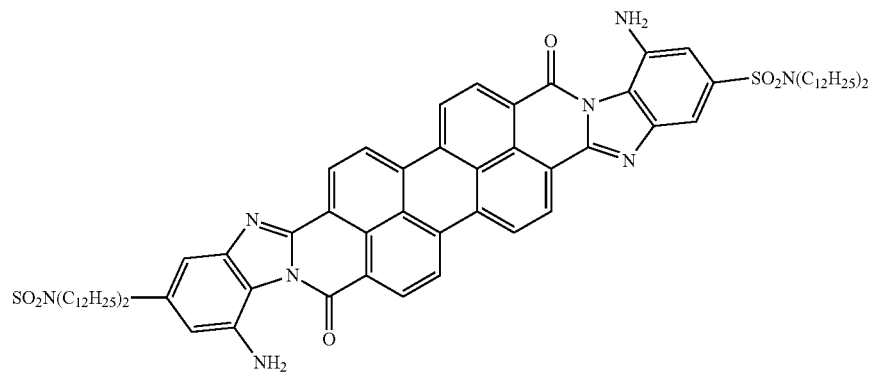
30
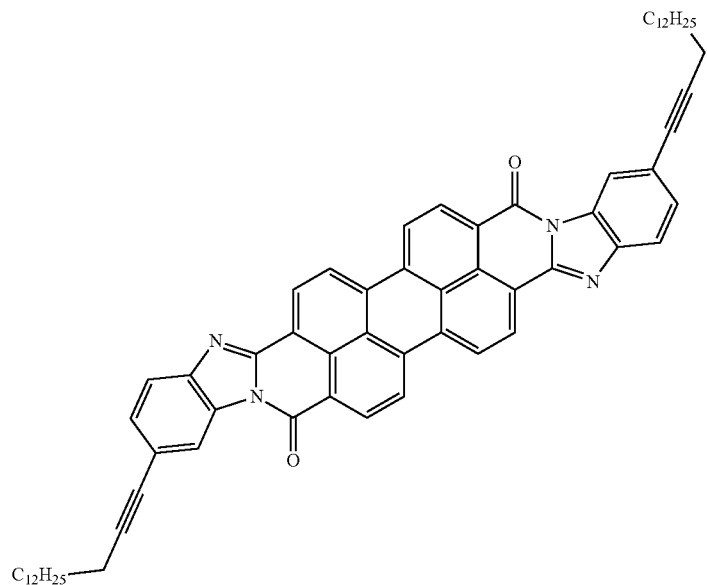

TABLE 5-continued

Examples of the organic compound

[Structure 31: Aromatic polycyclic core with two imide groups, substituted with two NO₂ groups and two alkynyl-C₁₂H₂₅ chains]

[Structure 32: Aromatic polycyclic core with two imide groups, substituted with two NO₂ groups and two alkynyl chains bearing C₉H₁₉ and C₁₁H₂₃ branches]

Structures 27 and 28 in Table 5 above are examples of structures in which $R_1$ groups are connected directly to the Core.

In an aspect, the present disclosure provides a dielectric layer comprising the disclosed organic compound. Further still, in some embodiments the dielectric layer comprises a mixture of embodiments of the disclosed organic compound. For example, in some embodiments the dielectric layer is comprised of regioisomers of the disclosed organic compound. In some embodiments, the dielectric layer is crystalline.

By way of example and not limitation, a crystal dielectric layer can be produced from the disclosed organic compound by Cascade Crystallization. For example, the symmetric arrangement of electrophilic groups (acceptors) and nucleophilic groups (donors) in the aromatic polycyclic conjugated core promotes formation of supramolecules.

Cascade Crystallization process involves a chemical modification step and four steps of ordering during the crystal dielectric layer formation. The chemical modification step introduces hydrophilic groups on the periphery of the molecule of the disclosed organic compound in order to impart amphiphilic properties to the molecule. Amphiphilic molecules stack together into supramolecules, which is the first step of ordering. At certain concentration, supramolecules are converted into a liquid-crystalline state to form a lyotropic liquid crystal, which is the second step of ordering. The lyotropic liquid crystal is deposited under the action of a shear force (or meniscus force) onto a substrate based on a Mayer Rod shearing technique, so that shear force (or the meniscus) direction determines the crystal axis direction in the resulting solid crystal layer. The external alignment upon the lyotropic liquid crystal, can be produced using any other means, for example by applying an external electric field at normal or elevated temperature, with or without additional illumination, magnetic field, or optical field (e.g., coherent photovoltaic effect); the degree of the external alignment should be sufficient to impart necessary orientation to the supramolecules of the lyotropic liquid crystal and form a structure, which serves as a base of the crystal lattice of the crystal dielectric layer. This directional deposition is third step of ordering, representing the global ordering of the crystalline or polycrystalline structure on the substrate surface. The last step of the Cascade Crystallization process is drying/crystallization, which converts the lyotropic liquid crystal into a solid crystal dielectric layer. The term Cascade Crystallization process is used to refer to the chemical modification and four ordering steps as a combination process.

The Cascade Crystallization process is used for production of thin crystalline dielectric layers. The dielectric layer produced by the Cascade Crystallization process has a global order which means that a direction of the crystallographic axis of the layer over the entire substrate surface is controlled by the deposition process. Molecules of the deposited material are packed into supramolecules with a limited freedom of diffusion or motion. The thin crystalline dielectric layer is characterized by an interplanar spacing of $3.4 \pm 0.3$ Å in the direction of one of the optical axes.

In another aspect, the present disclosure provides a capacitor, an example of which is shown in FIG. 1. The capacitor generally includes a first electrode (1), a second electrode (2), and a crystal dielectric layer (3) disposed between said first and second electrodes and wherein said crystal dielectric layer comprises sublayers (4) which are characterized by electronic polarizability and have supramolecules formed with the aromatic polycyclic conjugated Cores, of any of the types described herein, and isotropic insulating sublayers (5) formed with the A-groups which serve as the isolating groups described above. These insulating sublayers prevent occurrence of percolation with formation of continuous electrically conductive channels under action of electric field.

The electrodes 1, 2 may be more or less flat and planar and positioned more or less parallel to each other. Alternatively, the electrodes may be more or less planar and parallel, but not necessarily flat, e.g., they may coiled, rolled, bent, folded, or otherwise shaped to reduce the overall form factor of the capacitor. It is also possible for the electrodes to be non-flat, non-planar, or non-parallel or some combination of two or more of these. By way of example and not by way of limitation, a spacing d between the electrodes 1, 2 which may correspond to the thickness of the crystal dielectric layer 3 may range from about 10 nm to about 100 000 nm. As noted in Equation (2) above, the maximum voltage $V_{bd}$ between the electrodes 1, 2 is approximately the product of the breakdown field and the electrode spacing d. For example, if, $E_{bd}$=0.1 V/nm and the spacing d between the electrodes 1, 2 is 100 µm, the maximum voltage $V_{bd}$ would be 10,000 volts.

The electrodes 1, 2 may have the same shape as each other, the same dimensions, and the same area A. By way of example, and not by way of limitation, the area A of each electrode 1,2 may range from about 0.01 m$^2$ to about 1000 m$^2$. By way of example and not by way of limitation, for rolled capacitors, electrodes up to, e.g., 1000 m long and 1 m wide are manufacturable with roll-to-roll processes similar to those used to manufacture magnetic tape or photographic film.

These ranges are non-limiting. Other ranges of the electrode spacing d and area A are within the scope of the aspects of the present disclosure.

If the spacing d is small compared to the characteristic linear dimensions of electrodes (e.g., length and/or width), the capacitance C of the capacitor may be approximated by the formula:

$$C=\kappa\varepsilon_0 A/d, \qquad (3)$$

where $\varepsilon_o$ is the permittivity of free space (8.85×10$^{-12}$ Coulombs$^2$/(Newton·meter$^2$)) and κ is the dielectric constant of the dielectric layer. The energy storage capacity U of the capacitor may be approximated as:

$$U=\tfrac{1}{2}CV_{bd}^2 \qquad (4)$$

which may be rewritten using equations (2) and (3) as:

$$U=\tfrac{1}{2}\kappa\varepsilon_o A E_{bd}^2 d \qquad (5)$$

The energy storage capacity U is determined by the dielectric constant κ, the area A, and the breakdown field $E_{bd}$. By appropriate engineering, a capacitor or capacitor bank may be designed to have any desired energy storage capacity U. By way of example, and not by way of limitation, given the above ranges for the dielectric constant κ, electrode area A, and breakdown field $E_{bd}$ a capacitor in accordance with aspects of the present disclosure may have an energy storage capacity U ranging from about 500 Joules to about 2×10$^{16}$ Joules.

For a dielectric constant κ ranging, e.g., from about 100 to about 1,000,000 and constant breakdown field $E_{bd}$ between, e.g., about 0.1 and 0.5 V/nm, a capacitor of the type described herein may have a specific energy capacity per unit mass ranging from about 10 Wh/kg up to about 100,000 Wh/kg, though implementations are not so limited.

In order that aspects of the present disclosure may be more readily understood, reference is made to the following examples, which are intended to be illustrative of the invention, but are not intended to be limiting the scope.

Example 1

This Example describes synthesis of organic compound F:

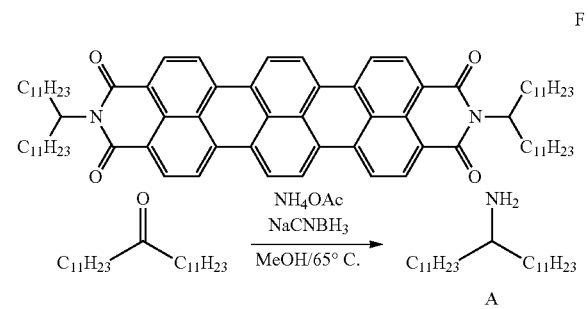

Synthesis of A: Tricosanone (100 g, 295 mmol, 1 eq.) and Ammonium acetate (NH$_4$OAc) (114 g, 77.1 mmol, 5 eq.) were added to a round bottom flask with 590 mL of Methanol. This mixture was heated to 65° C. After 1 hour, Sodium Cyanoborohydride (NaCNBH$_3$) (11.2 g, 117 mmol, 0.6 eq.) was slowly added over 30 min. The reaction was monitored by APCI mass spectrometry. Once the reaction was complete (1 hour), the reaction was extracted with 500 mL of Hexanes. The Hexanes layer was collected and washed with an additional 500 mL of water (H₂O). The organic layer was collected, dried with Magnesium sulfate (MgSO₄), filtered and the solvent was removed under reduced pressure to yield a viscous light-yellow oil. This oil was re-dissolved in 100 mL of Dichloromethane (DCM) and poured into 1000 mL of Methanol (MeOH). This solution was cooled to −20° C. for 2 days and A was collected by vacuum filtration as a white solid (88.8 g, 88%).

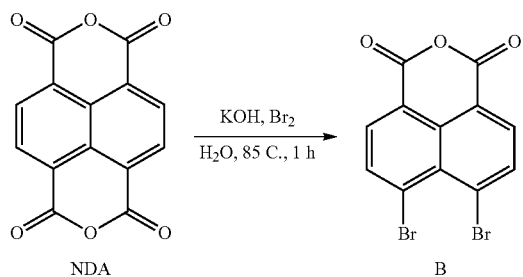

Synthesis of B: A round bottom flask was equipped with a magnetic stir bar, Naphthalene dianhydride (NDA) (50.0 g, 186 mmol, 1 eq.), Potassium Hydroxide (KOH) pellets (51.7 g, 932 mmol, 4.2 eq.), and H₂O (370 mL). This mixture was placed into a preheated oil bath set to 85° C. and vigorously stirred for 20 minutes, until the dispersion completely dissolved. To this was added Bromine (Br₂) (25 mL, 466 mmol), dropwise over the course of 2 hours. As Br₂ is added, CO₂ is released from the reaction and a yellow precipitate begins to form. Once all Br₂ has been added, the reaction was allowed to stir for an additional 1 hour after which the flask was removed from the heat and cooled to room temperature. The crude reaction mixture was poured into 400 mL of 2M aqueous Hydrochloric acid (HCl). The resulting precipitate was filtered under vacuum before being washed with 100 mL of H₂O and 300 mL of Methanol. The collected solid was dried under reduced pressure overnight to yield a light brown solid (58.9 g, 89%). The solid was used in the next step without further purification.

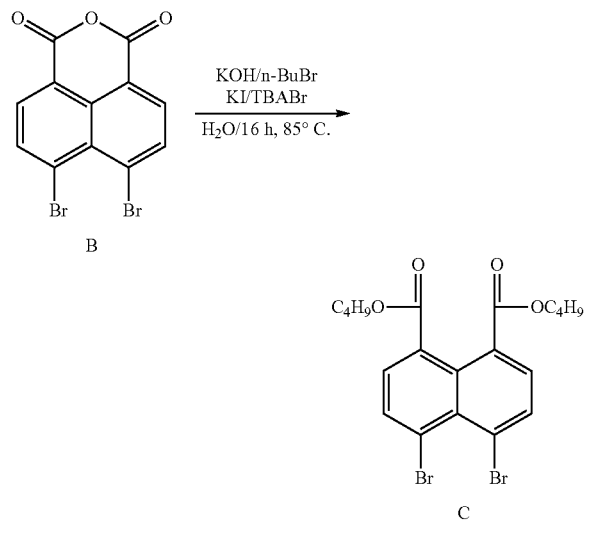

Synthesis of C: B (25.1 g, 70.2 mmol, 1 eq.) and KOH pellets (19.8 g, 300 mmol, 4.2 eq.) were added to a round bottom flask filled with 140 mL of H₂O. This mixture was heated to 85° C. until fully dissolved (20 min). To this mixture was added Potassium iodide (KI) (1.17 g, 7.02 mmol, 0.1 equivalent), Tetrabutylammonium Bromide (TBABr) (11.4 g, 35.3, 0.5 equiv.) and n-Butyl bromide (45.2 mL, 6 eq.). This mixture was allowed to stir at 85° C. for 16 h, and was monitored by TLC (75:25 Hexanes/Ethyl Acetate). Once the reaction was complete, it was removed from heat and cooled to room temperature. The crude reaction was extracted with DCM (3×100 mL), dried with MgSO₄, filtered and concentrated under reduced pressure. The crude reaction was filtered through a silica plug (25% Ethyl Acetate (EtOAc) in Hexanes) and solvent removed under reduced pressure. The crude mixture was dissolved in a minimum amount of warm hexanes and placed into a −20° C. freezer to precipitate overnight. The resulting solid was collected under vacuum filtration to isolate C as a light yellow solid (13.98, 41%).

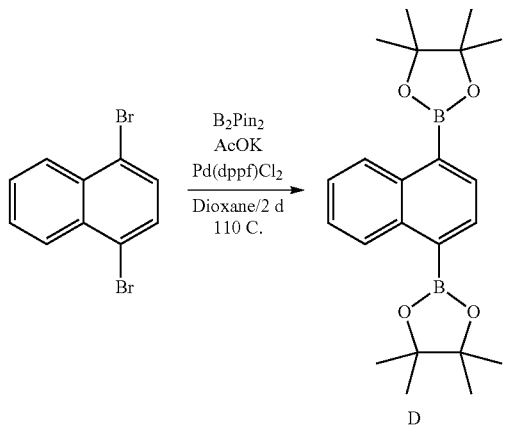

Synthesis of D: 1,4-dibromonaphthalene (25.1 g, 87.4 mmol, 1 eq.), Pd(dppf)Cl₂ (3.20 g, 4.37 mmol, 0.05 eq.), Potassium Acetate (AcOK) (25.74 g, 262 mmol, 3 eq.), and B₂Pin₂ (55.5 g, 218 mmol, 2.5 eq.) were added to round bottom flask. This mixture was then evacuated and back-filled with N₂ 3 times. In a separate flask, dioxane (170 mL) was bubbled with N₂ for 30 minutes. This degassed solvent was then added to the reaction flask under an N₂ atmosphere and placed into a preheated 110° C. oil bath. After 1 h, the reaction was removed from the oil bath and allowed to cool to room temperature before being washed with deionized H₂O (200 mL) and extracted using EtOAc (3×200 mL). The organic layers were collected, dried with MgSO₄, filtered, and the solvent was removed under reduced pressure. The crude product was triturated in 400 mL of methanol for 30 min and the solid collected by vacuum filtration to yield D (19.7 g, 59% yield).

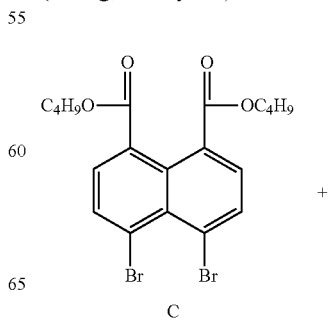

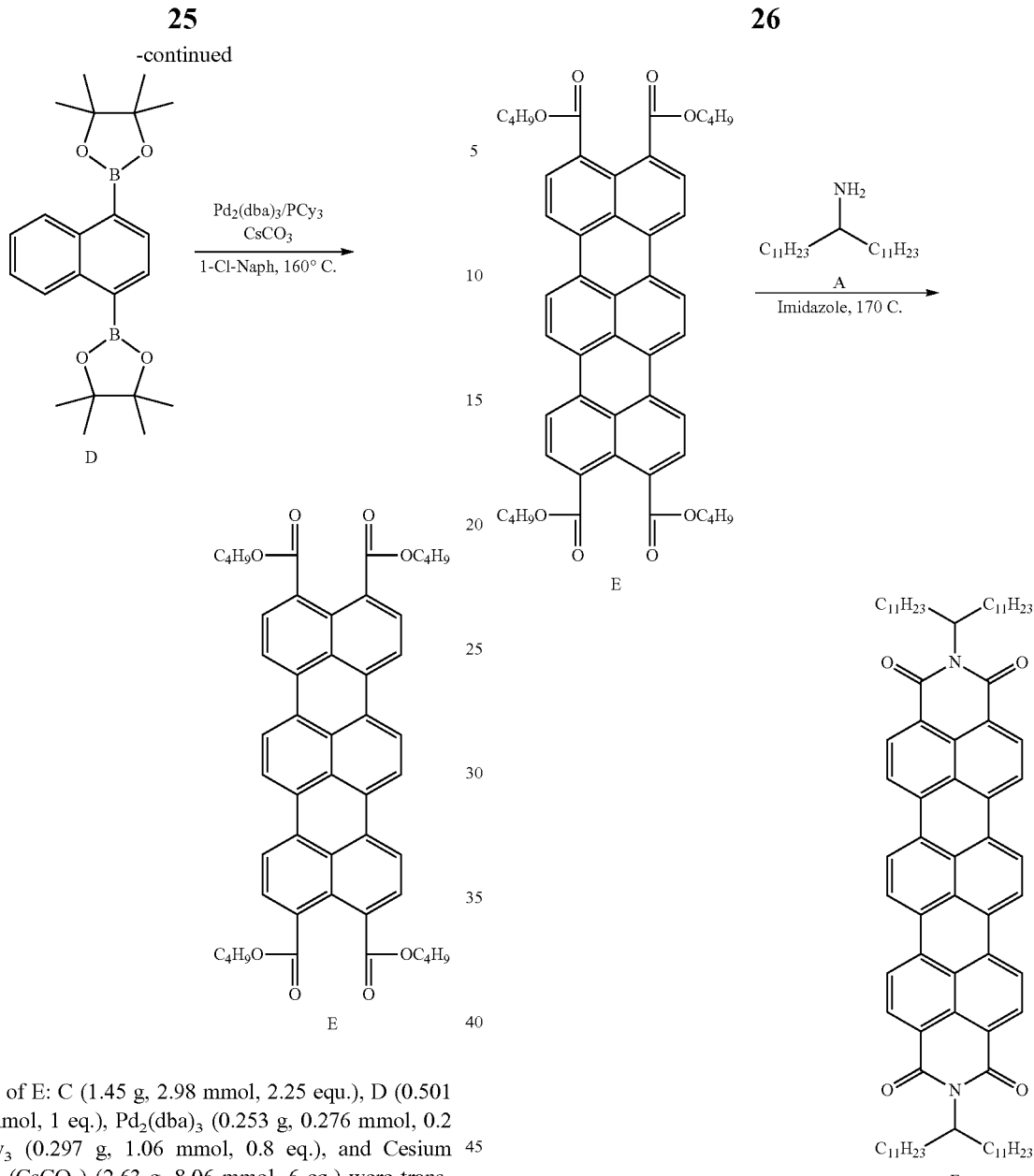

Synthesis of E: C (1.45 g, 2.98 mmol, 2.25 equ.), D (0.501 g, 1.32 mmol, 1 eq.), $Pd_2(dba)_3$ (0.253 g, 0.276 mmol, 0.2 eq.), $PCy_3$ (0.297 g, 1.06 mmol, 0.8 eq.), and Cesium carbonate ($CsCO_3$) (2.63 g, 8.06 mmol, 6 eq.) were transferred to a round bottom flask and purged with $N_2$. In a separate flask, 1-Chloronaphthalene (45 mL) was sparged for 30 min under a flow of $N_2$ before being added to the reaction flask. This mixture was put under vacuum for 10 minutes and once again backfilled with $N_2$ before being placed into a preheated oil bath set to 160° C. and stirred for 24 hours. Once the reaction was complete, the crude mixture was poured into 200 mL of hexanes and was passed through a silica plug using hexanes (200 mL) then 25% EtOAc in Hexanes (200 mL) until a purple band began to elute. This purple band was collected and eluted with an additional 200 mL of 1:1 Hexanes/EtOAc until completely collected. The solvent was removed under reduced pressure and re-dissolved into a minimum amount of Diethyl ether ($Et_2O$) (20 mL) and precipitated into 200 mL of methanol. This mixture was then placed into a −20° C. freezer for 2 hours and the dark purple solid was collected by vacuum filtration on a 0.2 m nylon filter (0.569 g, 55%).

Synthesis of F: To a round bottom flask equipped with a stir bar was added E (0.111 g, 0.125 mmol, 1 eq.), A (0.380 g, 1.12 mmol, 9 eq.), and imidazole (1.55 g, 22.8 mmol, 180 eq.). This mixture was purged with $N_2$ 3× then placed into a 170° C. oil bath and let to stir for 16 hours. The next morning the reaction has changed color from dark violet to dark blue. Once complete, the reaction was cooled to 100° C. and was washed with 10 mL of 2 M HCl and extracted with EtOAc (3×20 mL). The organic fractions were collected, dried with $MgSO_4$, filtered and solvent was removed under reduced pressure. The product was then purified by column chromatography (Hexanes→26% EtOAc in Hexanes). The blue fractions were collected, and solvent removed before being re-dissolved into a minimum amount of $CH_2Cl_2$ and precipitated into 40 mL of Methanol. The mixture was placed into a −20° C. freezer overnight and the blue resulting blue precipitate (F) was collected via vacuum filtration (0.069 g, 53%).

Example 2
This Example describes synthesis of the disclosed organic compound (see, general structural formula 41 in Table 5) according following structural scheme:
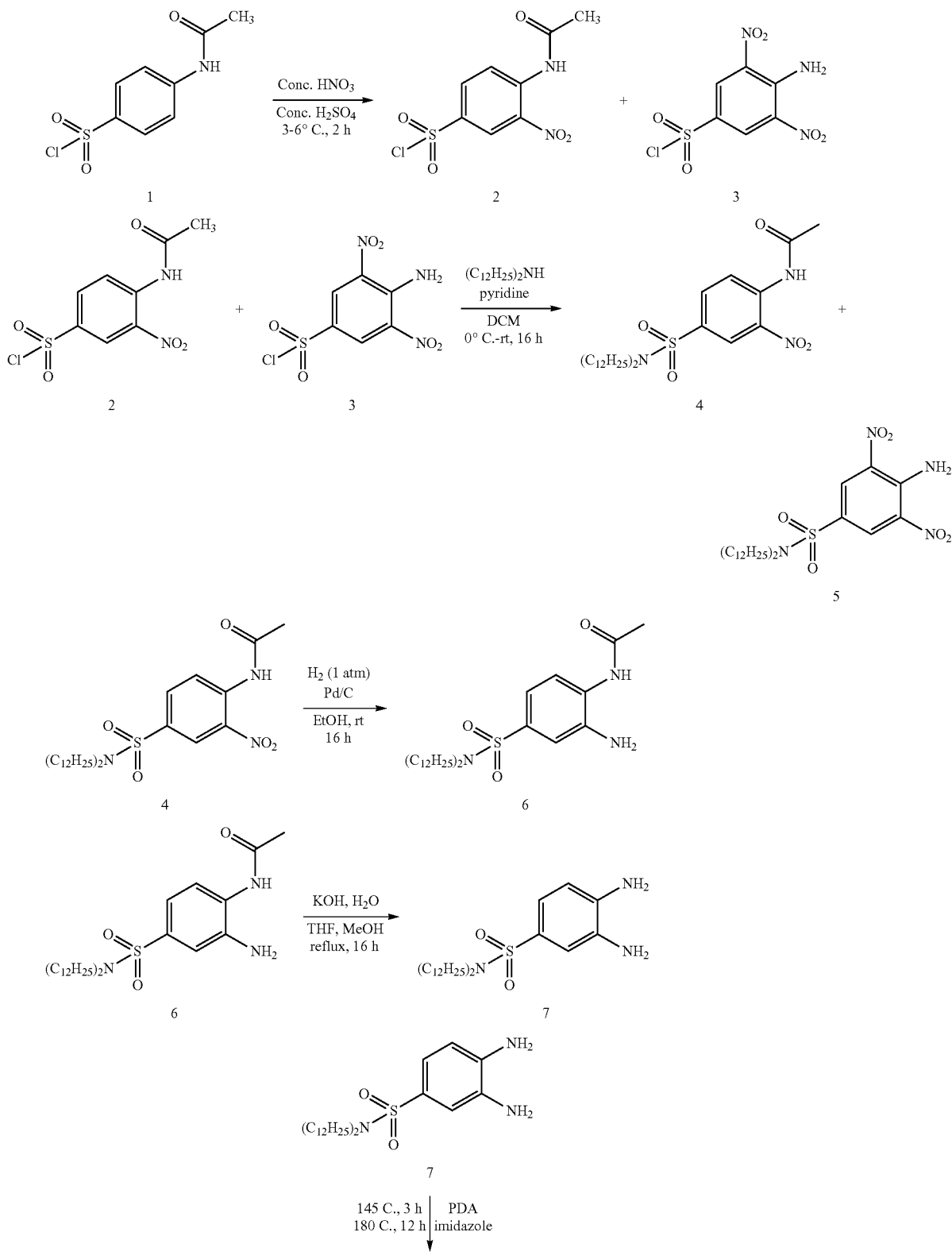

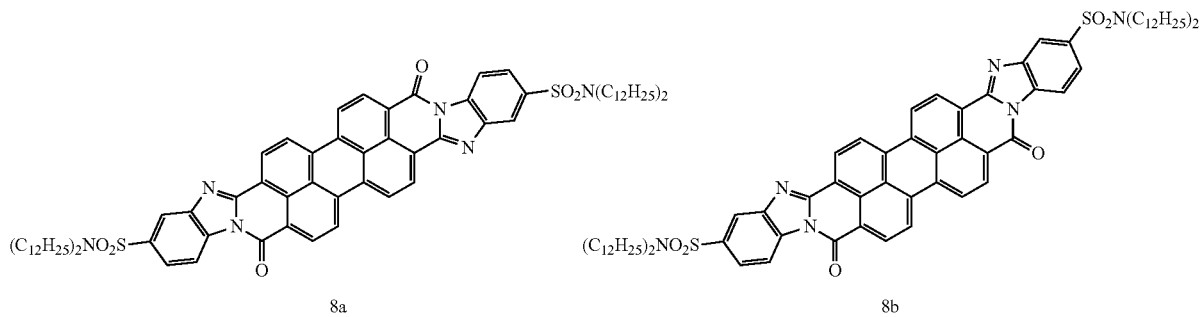

8a          8b

To a cooled (ice-water) concentrated $H_2SO_4$ (240 mL) was added Sulfonyl chloride 1 (50.0 g, 0.210 mol, 1.0 eq.) in portions. The mixture was stirred at 0° C. until a clear solution. A pre-mixed mixture of concentrated Sulfuric acid ($H_2SO_4$) (98%, 30.0 mL) and concentrated Nitric acid ($HNO_3$) (70%, 30.0 mL) was added slowly to maintain reaction temperature below 10° C. After addition, the reaction mixture was stirred at 10° C. for 4 h, poured into ice-water (2000 mL). The precipitate was brought into hot Benzene (60° C., 1000 mL), separated organic layer from water, dried over Sodium sulfate ($Na_2SO_4$), filtered and concentrated to give 47.0 g (77%) of a mixture mono-nitro compound 2 and bis-nitro 3•(2:3=3:2•by NMR). $^1$H NMR (300 MHz, $CDCl_3$) δ 10.67 (bs, 1H), 9.19-9.16 (d, J=9.0 Hz, 1H), 9.12 (s, 1H), 9.04 (bs, 2H), 8.91-8.90•(d, J=3.0 Hz, 1H), 8.26-8.22 (dd, J=9.0 Hz, J=3.0 Hz, 1H), 2.38 (s, 3H).

To a solution of Didodecylamine (25.0 g, 70.7 mmol, 1.0 eq.) in DCM (400 mL), was added pyridine (35.1 g, 440 mmol, 5.0 eq.) and a mixture of mono-nitro 2 and bis-nitro 3 (20.0 g, 68.9 mmol, 1.0 eq.) at 0° C. The resulting mixture was stirred at room temperature for 16 h, diluted with DCM (400 mL), washed with water (2×200 mL), brine (200 mL), dried over $Na_2SO_4$, filtered and concentrated to give a residue. The crude product was purified by flash chromatography column (from 30% to 50% EtOAc/Hexane) to give 6.3 g (15.4%) of mono-nitro compound 4 as a yellow solid and 11.0 g (26.7%) of bis-nitro 5 as a red-yellow solid. Compound 4: $^1$H NMR (300 MHz, $CDCl_3$) δ 10.50 (bs, 1H), 8.99-8.96 (d, J=9.0 Hz, 1H), 8.64 (s, 1H), 8.02-8.98 (d, J=10.8 Hz, 1H), 3.16-3.11 (t, J=7.8 Hz, 4H), 2.34 (s, 3H), 1.61-1.44 (m. 4H), 1.40-1.15 (m, 36H), 1.00-0.80 (t, J=6.0 Hz, 6H).

To a suspension of the mono-nitro compound 4 (6.30 g, 10.6 mmol, 1.0 eq.) in Ethanol (700 mL) was added Pd/C (10% on carbon, 50% wet, 1.3 g, 10 w %). The mixture was degassed (vacuum and fill with $H_2$) three times, and stirred at room temperature under 1 atm $H_2$ for 16 h, filtered through Celite. The filtrate was concentrated to give 6.0 g (100%) of the amine 6 as a yellow solid. $^1$H•NMR•(300•MHz, $CDCl_3$) δ 7.41-7.38 (d, J=8.1 Hz, 1H), 7.32 (bs, 1H), 7.20 (s, 1H), 7.18-7.15 (dd, J=8.4 Hz, J=1.8 Hz, 1H), 3.95 (bs, 2H), 3.08-3.03 (t, J=7.5 Hz, 4H), 1.45-1.40 (m, 4H), 1.35-1.15 (m, 36H), 0.92-0.80 (t, J=6.3 Hz, 6H).

To a solution of the amine 6 (6.00 g, 10.6 mmol, 1.0 eq.) in THF (30 mL) and MeOH (30 mL) was added a solution of KOH (6.00 g, 110 mmol, 10 eq.) in water (5.0 mL). The mixture was stirred at reflux for 6 h and concentrated. The residue was partitioned between EtOAc (100 mL) and water (100 mL). The organic layer was separated, dried over $Na_2SO_4$, filtered and concentrated to give a residue. The crude product was purified by flash chromatography column (50% EtOAc/Hexane) to give 3.5 g (63.1%) of diamine 7 as a light yellow solid. $^1$H NMR (300 MHz, $CDCl_3$) δ 7.18-7.14 (dd, J=7.8 Hz, J=1.8 Hz, 1H), 7.12 (s, 1H), 6.72-6.69 (d, J=8.1 Hz, 1H), 3.07-3.02 (t, J=7.2 Hz, 4H), 1.45-1.40 (m, 4H), 1.35-1.15 (m, 36H), 1.00-0.80 (t, J=6.0 Hz, 6H).

The diamine 7 (3.40 g, 6.50 mmol, 2.2 eq.), 3,4,9,10-Perylenetetracarboxylic dianhydride (PDA) (1.20 g, 2.90 mmol, 1.0 eq.) and Imidazole (31.0 g, 455 mmol, 70 eq.) were mixed well in a 200 mL round-bottom flask equipped with a rotavap bump guard. The mixture was degassed (vacuum and fill with $N_2$) three times and stirred at 145° C. for 3 h, 180° C. for 12 h. After cooling to room temperature, the reaction mixture was crushed into water (500 mL), stirred for 1 hour, and filtered through a filter paper to collected precipitate which was washed with water (4×50 mL) and Ethanol (4×50 mL), dried on a high vacuum to give 3.7 g (91.5%) of the diamidine isomers 8a and 8b as a dark purple solid. $^1$H NMR (300 MHz, $CDCl_3$) δ 8.80-8.40 (m, 8H), 8.22-8.06 (m, 2H), 7.70-7.60 (m, 4H), 3.20-3.00 (m, 8H), 1.60-1.40 (m, 8H), 1.40-1.10 (m, 72H), 0.96-0.80 (m, 12H).

Example 3

This example describes synthesis of the disclosed organic compound (see, general structural formula 42 in Table 5) according following structural scheme:

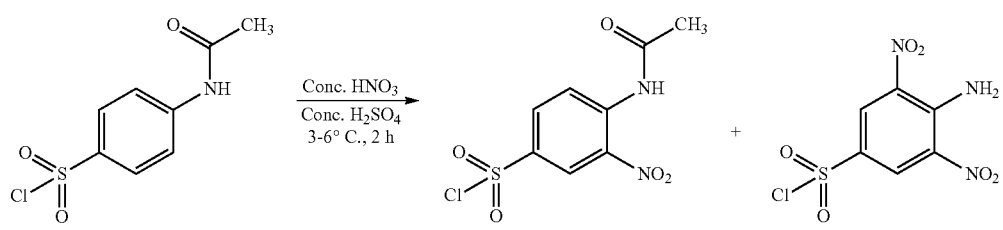

2        3

-continued

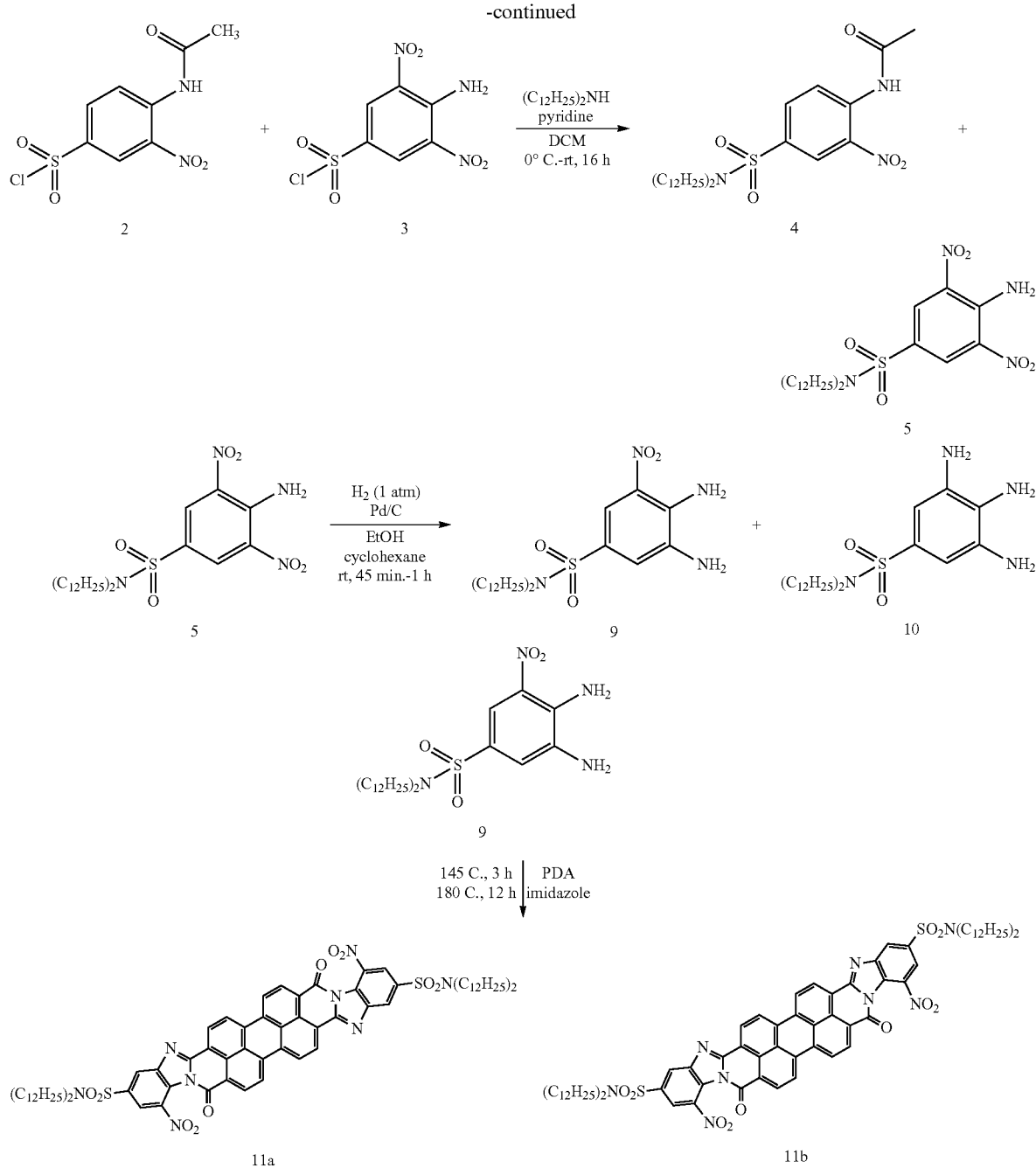

Sulfonyl chloride 1 (50.0 g, 0.21 mol, 1.0 eq.) was added in portions to cooled (ice-water) concentrated H$_2$SO$_4$ (240.0 mL). The mixture was stirred at 0° C. until a clear solution. A pre-mixed mixture of concentrated H$_2$SO$_4$ (98%, 30.0 mL) and concentrated HNO$_3$ (70%, 30.0 mL) was added slowly to maintain reaction temperature below 10° C. After addition, the reaction mixture was stirred at 10 C for 4 h, poured into ice-water (2000 mL). The precipitate was brought into hot Benzene (60° C., 1000 mL), separated organic layer from water, dried over Na$_2$SO$_4$, filtered and concentrated to give 47.0 g (77%) of a mixture mono-nitro compound 2 and bis-nitro compound 3 (2:3=3:2 by NMR). $^1$H NMR (300 MHz, CDCl$_3$) δ 10.67 (bs, 1H), 9.19-9.16 (d, J=9.0 Hz, 1H), 9.12 (s, 1H), 9.04 (bs, 2H), 8.91-8.90 (d, J=3.0 Hz, 1H), 8.26-8.22 (dd, J=9.0 Hz, J=3.0 Hz, 1H), 2.38 (s, 3H).

To a solution of Didodecylamine (25.0 g, 70.7 mmol, 1 eq.) in DCM (400 mL), was added Pyridine (35.1 g, 440 mmol, 5.0 eq.) and a mixture of mono-nitro 2 and bis-nitro 3 (20.0 g, 68.9 mmol, 1.0 eq.) at 0° C. The resulting mixture was stirred at room temperature for 16 h, diluted with DCM (400 mL), washed with water (2×200 mL), brine (200 mL), dried over dried over Na$_2$SO$_4$, filtered and concentrated to give a residue. The crude product was purified by flash chromatography column (30% to 50% EtOAc/Hexane) to give 6.3 g (15.4%) of mono-nitro compound 4 as a yellow solid and 11.0 g (26.7%) of bis-nitro 5 as a red-yellow solid.

5: $^1$H NMR (300 MHz, CDCl$_3$) δ 8.89 (s, 2H), 8.76 (bs, 2H), 3.18-3.13 (t, J=7.5 Hz, 4H), 2.34 (s, 3H), 1.61-1.44 (m, 4H), 1.40-1.15 (m, 36H), 0.90-0.80 (t, J=6.3 Hz, 6H).

To a solution of the Bis-nitro compound 5 (8.60 g, 14.4 mmol, 1.0 eq.) in ethanol (800 mL) and cyclohexane (800 mL) was added Pd/C (10% on carbon, 50% wet, 0.9 g, 5 w %). The mixture was degassed (vacuum and fill with H$_2$) three times, and stirred at room temperature under 1 atm H$_2$ for 1 h, filtered through Celite. The filtrate was concentrated to give 4.5 g (55.0%) of the diamine 9 as a yellow-red solid, and 2.3 g of an intermediate as a yellow solid which was hydrogenated again following the above procedure to give 1.3 g (16.8%) of the Triamine 10 as a dark-brown solid. Compound 9: $^1$H NMR (300 MHz, CDCl$_3$) δ 8.18 (s, 1H), 7.28 (s, 1H), 6.38 (s, 2H), 3.62 (s, 2H), 3.12-3.06 (t, J=8.6 Hz, 4H), 1.60-1.45 (m, 4H), 1.38-1.15 (m, 36H), 0.92-0.82 (t, J=6.3 Hz, 6H).

Diamine 9 (4.50 g, 7.90 mmol, 2.2 eq.), 3,4,9,10-Perylenetetracarboxylic dianhydride (1.40 g, 3.60 mmol, 1.0 eq.) and Imidazole (38.0 g, 550 mmol, 70 eq.) were into a 200 mL round-bottom flask equipped with a rotavap bump guard. The mixture was degassed (vacuum and fill with N$_2$) three times and stirred at 145° C. for 3 hrs, 180° C. for 12 hrs. After cooling to rt, the reaction mixture was crushed into water (600 mL), stirred for 1 hour, and filtered through a filter paper to collected precipitate which was washed with water (4×50 mL) and Ethanol (4×50 mL), dried on a high vacuum to give 5.2 g (99.0%) of the diamidine isomers 11a and 11b as a dark purple solid.

Example 4

This example describes synthesis of the disclosed organic compound (see, general structural formula 43 in Table 5) according following structural scheme:

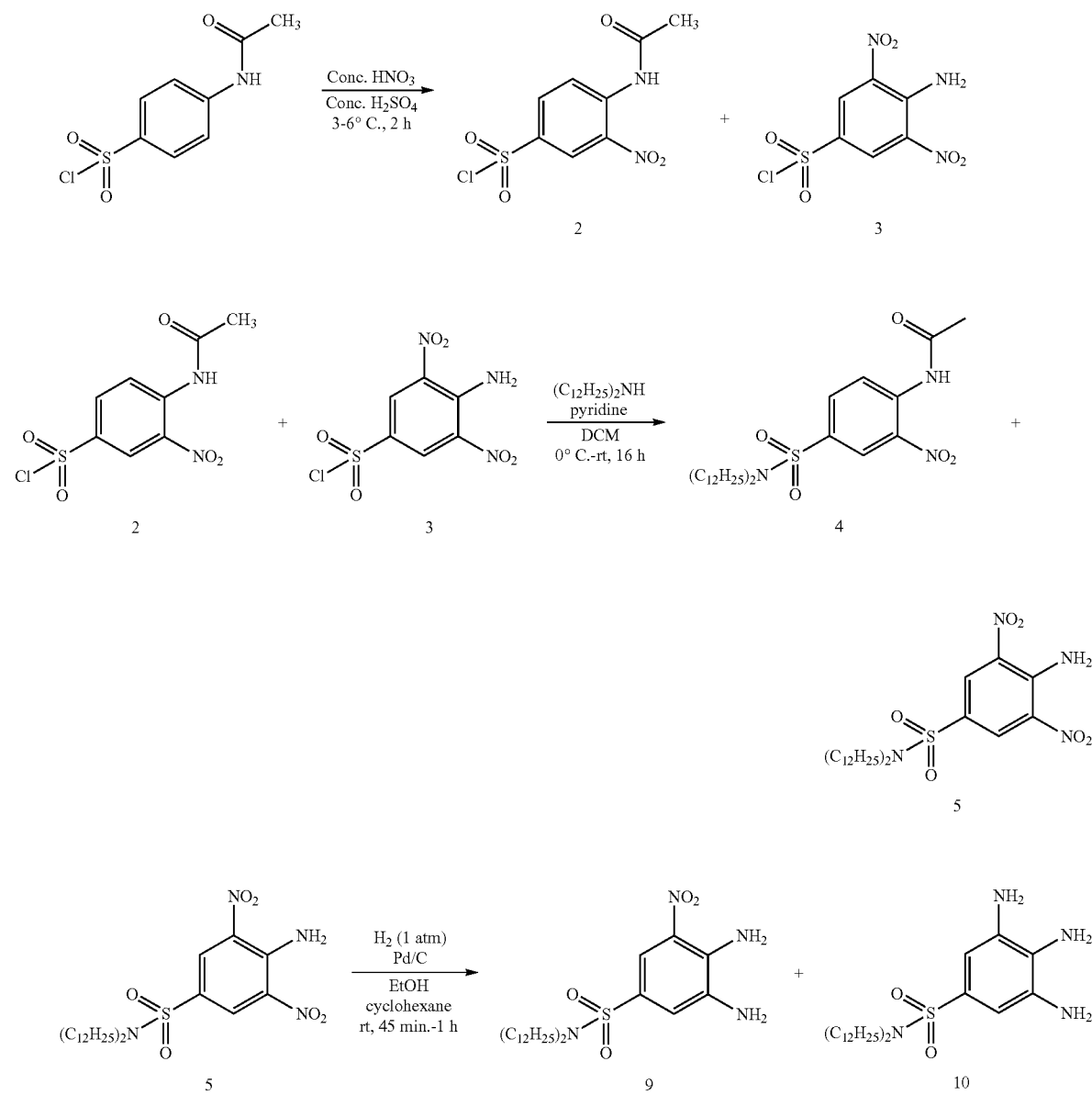

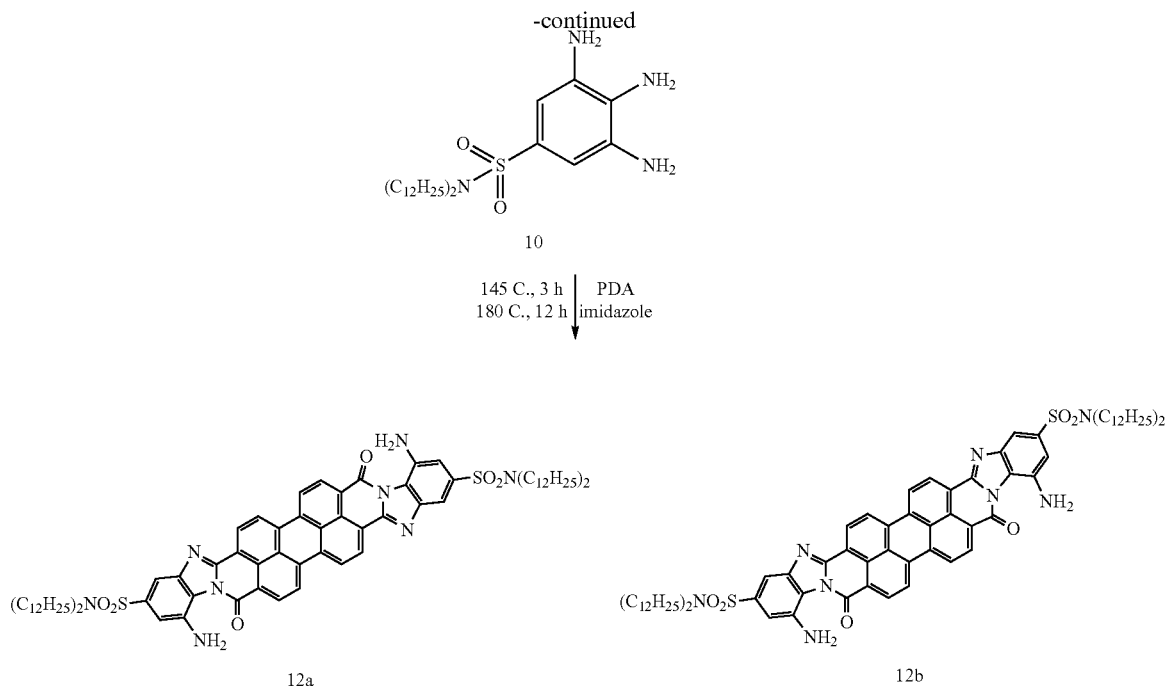

To a cold (ice-water) concentrated H₂SO₄ (240 mL) was added Sulfonyl chloride 1 (50.0 g, 0.210 mol, 1.0 eq.) in portions. The mixture was stirred at 0° C. until a clear solution. A pre-mixed mixture of concentrated H₂SO₄ (98%, 30.0 mL) and concentrated HNO₃ (70%, 30.0 mL) was added slowly to maintain reaction temperature below 10° C. After addition, the reaction mixture was stirred at 10° C. for 4 h, poured into ice-water (2000 mL). The precipitate was brought into hot benzene (60° C., 1000 mL), separated organic layer from water, dried over Na₂SO₄, filtered and concentrated to give 47.0 g (77%) of a mixture mono-nitro compound 2 and bis-nitro compound 3 (2:3=3:2 by NMR). $^1$H NMR (300 MHz, CDCl₃) δ 10.67 (bs, 1H), 9.19-9.16 (d, J=9.0 Hz, 1H), 9.12 (s, 1H), 9.04 (bs, 2H), 8.91-8.90 (d, J=3.0 Hz, 1H), 8.26-8.22 (dd, J=9.0 Hz, J=3.0 Hz, 1H), 2.38 (s, 3H).

To a solution of Didodecylamine (25.0 g, 70.7 mmol, 1 eq.) in dichloromethane (400 mL), was added pyridine (35.1 g, 440 mmol, 5.0 eq). and a mixture of mono-nitro 2 and bis-nitro 3 (20.0 g, 68.9 mmol, 1.0 eq) at 0° C. The resulting mixture was stirred at room temperature for 16 h, diluted with DCM (400 mL), washed with water (2×200 mL), brine (200 mL), dried over dried over Na₂SO₄, filtered and concentrated to give a residue. The crude product was purified by flash chromatography column (30% to 50% EtOAc/Hexane) to give 6.3 g (15.4%) of mono-nitro compound 4 as a yellow solid and 11.0 g (26.7%) of bis-nitro 5 as a red-yellow solid. 5: $^1$H NMR (300 MHz, CDCl₃) δ 8.89 (s, 2H), 8.76 (bs, 2H), 3.18-3.13 (t, J=7.5 Hz, 4H), 2.34 (s, 3H), 1.61-1.44 (m, 4H), 1.40-1.15 (m, 36H), 0.90-0.80 (t, J=6.3 Hz, 6H).

To a solution of the bis-nitro compound 5 (8.60 g, 14.4 mmol, 1.0 eq.) in Ethanol (800 mL) and Cyclohexane (800 mL) was added Pd/C (10% on carbon, 50% wet, 0.9 g, 5 w %). The mixture was degassed (vacuum and fill with H₂) three times, and stirred at room temperature under 1 atm H₂ for 1 hour, filtered through Celite. The filtrate was concentrated to give 4.5 g (55.0%) of the diamine 9 as a yellow-red solid, and 2.3 g of an intermediate as a yellow solid which was hydrogenated again following the above procedure to give 1.3 g (16.8%) of the triamine 10 as a dark-brown solid. Compound 10: H NMR (300 MHz, CDCl₃) δ 6.77 (s, 2H), 3.55-3.35 (m, 6H), 3.06-3.00 (t, J=7.5 Hz, 4H), 1.55-1.42 (m, 4H), 1.38-1.18 (m, 36H), 0.90-0.86 (t, J=6.3 Hz, 6H), 2.98-2.94 (m, 2H), 2.68-2.64 (m, 2H), 2.60 (s, 3H), 2.30 (s, 3H).

Diamine 10 (0.50 g, 0.880 mmol, 2.2 e.), 3,4,9,10-Perylenetetracarboxylic dianhydride (0.16 g, 0.40 mmol, 1.0 eq) and Imidazole (4.2 g, 61.6 mmol, 70 eq to diamine) were added into a 100 mL round-bottom flask equipped with a rotavap bump guard. The mixture was degassed (vacuum and fill with N₂) three times and stirred at 145° C. for 3 h, 180° C. for 12 h. After cooling to rt, the reaction mixture was crushed into water (200 mL), stirred for 1 hour, and filtered through a filter paper to collected precipitate which was washed with water (4×30 mL) and Ethanol (4×30 mL), dried on a high vacuum to give 0.5 g (89.5%) of the diamidine isomers 12a and 12b as a dark solid.

Example 5

This example describes synthesis of the disclosed organic compound (see, general structural formula 44 in Table 5) according following structural schemes:

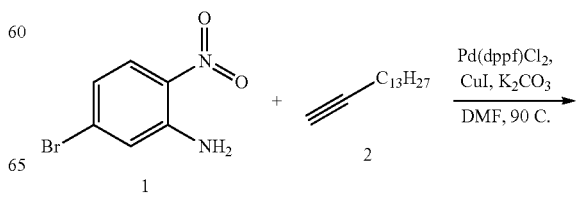

-continued

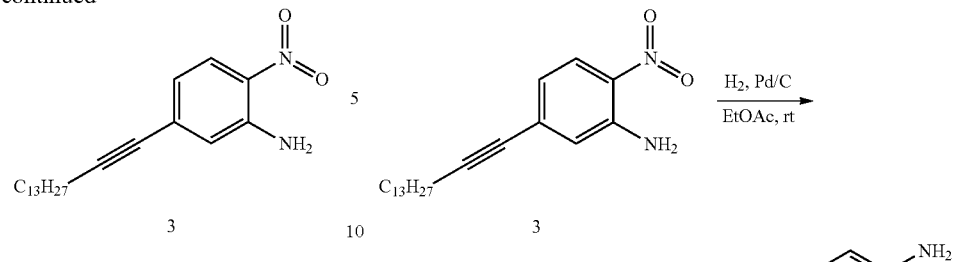

To anhydrous DMF (15.0 mL) was added compound 1 (3.30 g, 150 mmol, 1.0 eq.), compound 2 (4.80 mL, 180 mmol, 1.2 eq.), Pd(dppf)Cl$_2$ (0.240 g, 0.300 mmol, 0.02 eq.), Copper Iodide (I) (CuI) (0.120 g, 0.600 mmol, 0.04 eq.) and K$_2$CO$_3$ (4.20 g, 300 mmol, 2.0 eq.). The mixture was degassed under vacuum and purged with N$_2$ three times. The reaction was stirred at 90° C. for 8 hrs. The mixture was cooled down and Ethyl acetate (15 mL) was added to dilute. The solid was filtered. The filtrate was poured into water, extracted with Ethyl acetate (3×10 mL). It was sashed organic phase with water (10 mL) and brine (10 mL), dried over MgSO$_4$, filtered and concentrated. The residue was treated with a silica gel column to give 2.1 g (40%) of product 3 as a dark yellow solid. $^1$H NMR (300 MHz, CDCl$_3$) δ 8.17 (s, 1H), 7.34 (d, 1H), 6.70 (d, 1H), 6.19 (s, 2H), 2.36 (t, 2H), 1.26-1.56 (m, 22H), 0.87 (t, 3H).

To Ethyl Acetate (2.0 mL) was added compound 3 (500 mg, 1.44 mmol, 1.0 eq). and Pd/C (50.0 mg, 0.1 eq). The mixture was stirred at room temperature under H$_2$-balloon for 20 min. The solid was filtered off. The solution was concentrated to give compound 4 346 mg (80%) as light yellow solid. $^1$H NMR (300 MHz, CDCl$_3$) δ 6.61 (d, 1H), 6.50 (d, 1H), 6.54 (s, 1H), 7.86 (t, 2H), 1.25 (m, 22H), 0.88 (t, 3H).

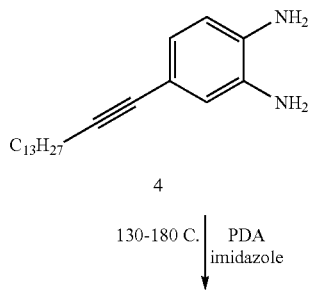

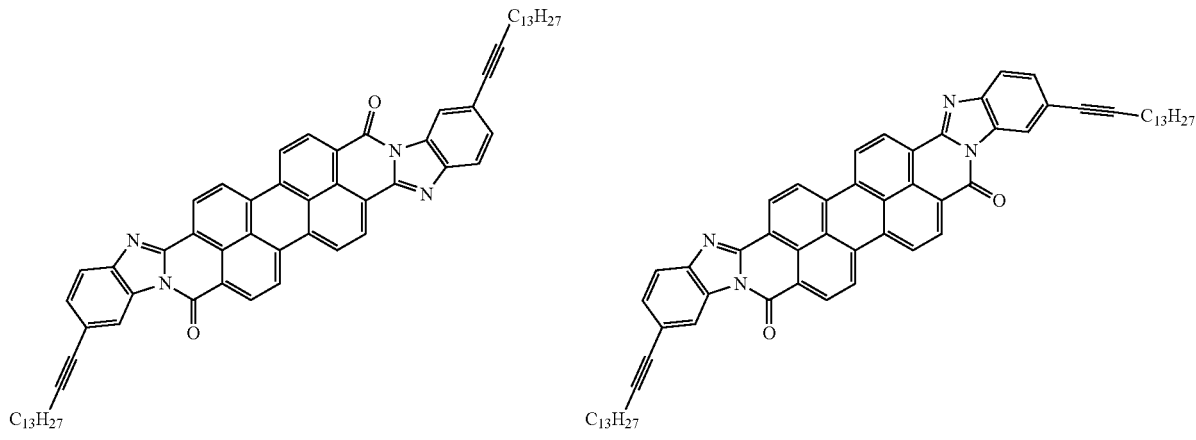

To a 25 mL flask was added compound 4 (758 mg, 2.40 mmol, 2.2 eq.), PDA (429 mg, 1.10 mmol, 1 eq.) and Imidazole (5.20 g, 77.0 mmol, 70 eq.). The mixture was degassed under vacuum and purged with N₂ three times. The reaction was stirred at 130° C. for 3 h and 180° C. for 12 h. The dark purple mixture was cooled down. The solid was washed with water (3×2 mL) and EtOH (3×2 mL), vacuum dried to give product 5a and 5b 912 mg (40%) as a dark purple solid. ¹H NMR (300 MHz, CDCl₃) not available.

Example 6

This example describes synthesis of the disclosed organic compound (see, general structural formula 46 in Table 5) according following structural schemes:

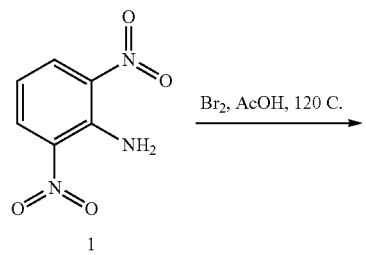

Compound 1 (5.00 g, 27.3 mmol, 1 eq.) was suspended in Acetic acid (AcOH) (50 mL). Br₂ (1.50 mL, 30.0 mmol, 1.1 eq.) was added dropwise at room temperature. After addition, the temperature was increased to 120° C. and kept stirring at this temperature for 2 h. The mixture was poured into ice water. The precipitate was filtered, washed with water and dried under vacuum to give product 2 6.8 g (95%) as a yellow solid.

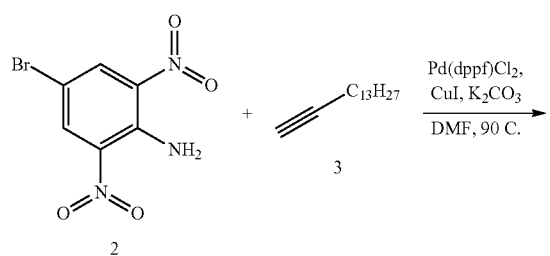

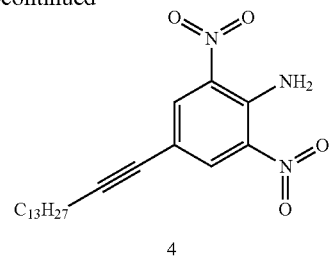

To anhydrous DMF (10.0 mL) was added compound 2 (2.00 g, 7.60 mmol, 1.0 eq.), compound 3 (2.40 mL, 9.10 mmol, 1.2 eq.), Pd(dppf)Cl₂ (0.130 g, 0.150 mmol, 0.02 eq), CuI (60.0 mg, 0.300 mmol, 0.04 eq.) and K₂CO₃ (2.10 g, 15.0 mmol, 2.0 eq.). The mixture was degassed under vacuum and purged with N₂ three times. The reaction was stirred at 90° C. for 8 h. The mixture was cooled down and Ethyl acetate (10 mL) was added to dilute. Filtered off the solid and poured the filtrate into water, extracted with Ethyl acetate (3×5 mL). Washed organic phase with water (5 mL) and brine (5 mL), dried over MgSO₄, filtered and concentrated. The residue was treated with a sil-gel column to give 520 mg (17%) of product 4 as a dark yellow solid. ¹H NMR (300 MHz, CDCl₃) δ 8.53 (s, 2H), 2.37 (t, 2H), 1.26-1.55 (m, 22H), 0.87 (t, 3H).

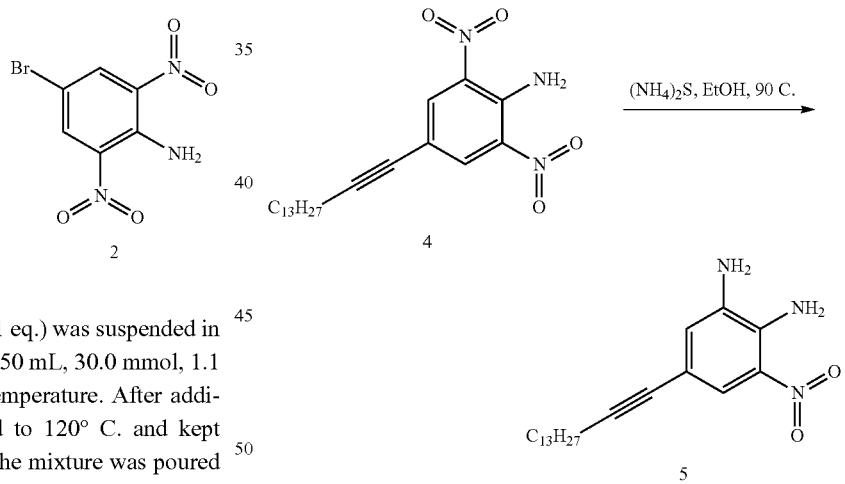

To EtOH (1.0 mL) was added compound 4 (60.0 mg, 0.150 mmol, 1.0 eq.) and ammonium sulfide (104 mg 20% water solution, 0.300 mmol, 2.0 eq.). The mixture was stirred at 80° C. for 1 h. Additional ammonium sulfide (104 mg 20% water solution, 0.300 mmol, 2.0 eq.) was added. The mixture was stirred at 80° C. for 1 h. The mixture was concentrated, diluted with Ethyl acetate, washed with water and brine. The organic phase was collected, concentrated and separated through a silicagel column to give product 5 21.8 mg (40%) as a dark red solid. ¹H NMR (300 MHz, CDCl₃) δ 7.81 (s, 1H), 6.94 (s, 1H), 6.03 (s, 2H), 3.26 (s, 2H), 2.36 (t, 2H), 1.26-1.53 (m, 22H), 0.87 (t, 3H).

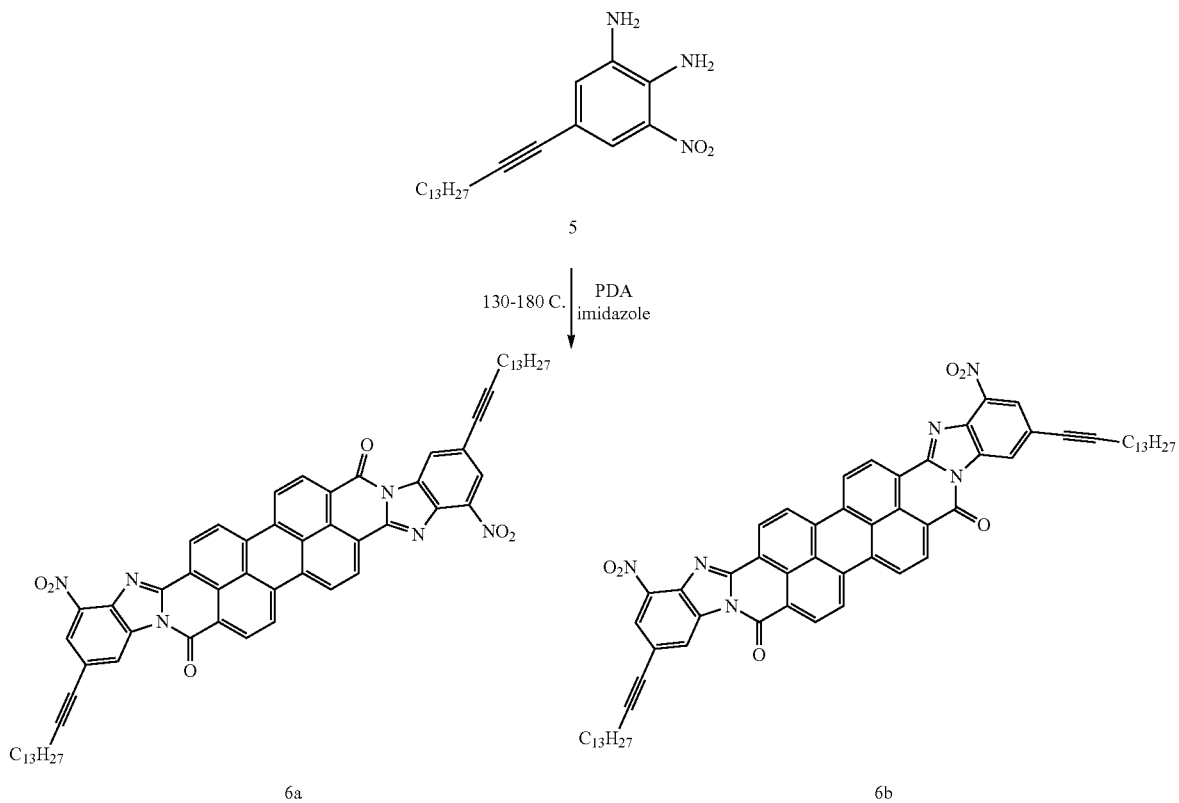

To a 5 mL vial was added compound 5 (21.8 mg, 0.0600 mmol, 2.2 eq.), PDA (10.8 mg, 0.0280 mmol, 1 eq.) and Imidazole (131 g, 1.93 mmol, 70 eq). The mixture was degassed under vacuum and purged with N₂ three times. The reaction was stirred at 130° C. for 3 h and 180° C. for 12 h. The dark purple mixture was cooled down. The solid was washed with water (3×0.5 mL) and EtOH (3×0.5 mL), vacuum dried to give products 6a and 6b 27 mg (45%) as a dark purple solid.

Example 7

This example describes synthesis of the disclosed organic compound (see, general structural formula 46 in Table 5) according following structural schemes:

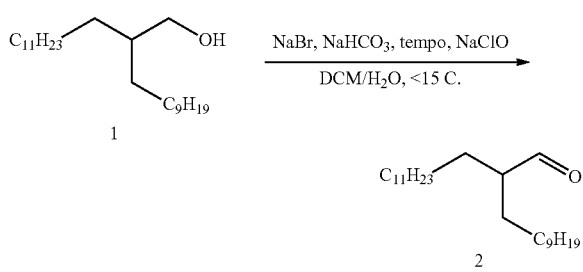

To H₂O (10.0 mL) was added NaHCO₃ (1.70 g, 20.2 mmol) and Sodium bromide (NaBr) (280 mg, 2.70 mmol). The mixture was stirred to form a clear solution. Compound 1 (20.0 g, 56.4 mmol, 1 eq.) in DCM (70 mL) and 2,2,6,6-Tetramethylpiperidine 1-oxyl (TEMPO) (340 mg) were added to the solution. The two-phase mixture was cooled down to 10° C. The Sodium hypochloride (NaClO) solution (70.5 mL, 0.8 N, 1 eq) was added dropwise with vigorously stirring. After addition, removed ice bath and kept stirring at room temperature for 30 min. The organic phase was collected. The aqueous phase was extracted with DCM (25 mL×2). All the organic fractions were collected, washed with water and brine, dried over MgSO₄ and concentrated to give compound 2 (18 g, 90%) as a colorless oil.

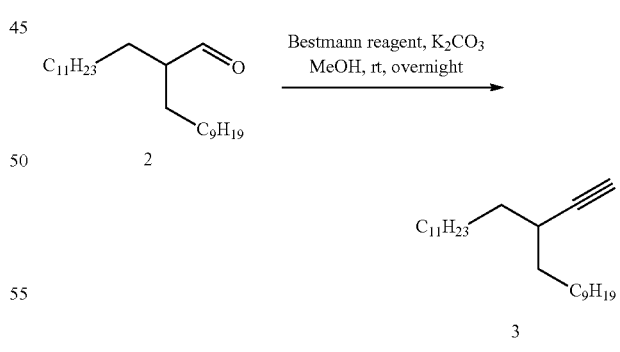

To MeOH (60 mL) was added freshly made compound 2 (18.0 g, 51.1 mmol, 2.0 eq.), Dimethyl (1-diazo-2-oxopropyl)phosphonate solution (Bestmann reagent) (5.00 g, 25.6 mmol, 1.0 eq) and K₂CO₃ (7.10 g, 51.1 mmol, 2.0 eq). The mixture was stirred at room temperature for 24 h. Ethyl acetate (30 mL) was added to dilute the mixture. The mixture was filtered to remove the precipitate, and washed with Ethyl acetate. The filtrate was concentrated. The residue was separated through a silicagel column to afford compound 3 7.4 g (82%) as white solid. ¹H NMR (300 MHz, CDCl₃) δ 2.15 (m, 1H), 2.03 (s, 1H), 1.26-1.41 (m, 40H), 0.87 (t, 6H).

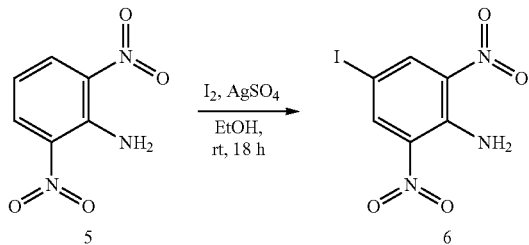 [SMILES: Nc1c([N+](=O)[O-])cccc1[N+](=O)[O-] ; Nc1c([N+](=O)[O-])cc(I)cc1[N+](=O)[O-]]

To EtOH (40.0 mL) was added compound 5 (4.20 g, 23.0 mmol, 1.0 eq.), Silver sulfate (AgSO₄) (10.0 g, 32.1 mmol, 1.4 eq.) and Iodide (I₂) (8.20 g, 32.1 mmol, 1.4 eq.). The mixture was stirred at room temperature for 18 h. The mixture was filtered to separate solid sediment (precipitate) and washed with Ethyl acetate. The filtrate was concentrated. The residue was separated through a silicagel column to afford compound 6 5.4 g (77%) as a dark yellow solid.

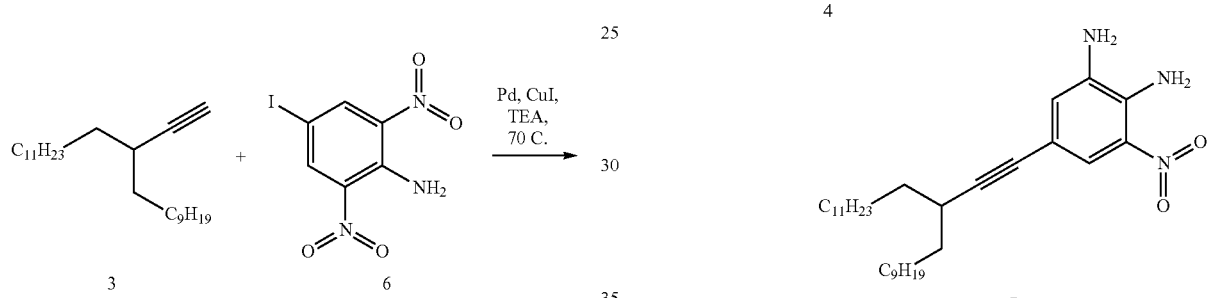

To anhydrous Tetrahydrofuran (THF) (10 mL) and Triethylamine (TEA) (10.0 mL) was added compound 3 (7.40 g, 21.2 mmol, 1.2 eq.), compound 6 (5.20 g, 16.7 mmol, 1.0 eq.), Pd(dppf)Cl₂ (50.0 mg, 0.0800 mmol, 0.02 eq.), CuI (20.0 mg, 0.1 mmol, 0.04 eq.). The mixture was degassed under vacuum and purged with N₂ three times. The reaction was stirred at 70° C. for 8 h. The mixture was cooled down and Ethyl acetate (10 mL) was added. The solid was filtered off. The filtrate was concentrated, and the residue was separated with a silicagel column to afford compound 4 7.5 g (84%) as a yellow solid. ¹H NMR (300 MHz, CDCl₃) δ 7.99 (s, 2H), 2.45 (m, 1H), 1.26-1.55 (m, 40H), 0.87 (t, 6H).

To EtOH (20.0 mL) was added compound 4 (7.50 g, 14.1 mmol, 1.0 eq.) and Ammonium sulfide (8.60 g, 20% water solution, 28.2 mmol, 2.0 eq.). The mixture was stirred at 80° C. for 1 h. Additional Ammonium sulfide (8.60 g, 20% water solution, 28.2 mmol, 2.0 eq.) was added. The received mixture again was stirred at 80° C. for 1 h. The mixture was concentrated, diluted with ethyl acetate, washed with water and brine. The organic phase was collected, concentrated and separated through a silicagel column to give product 7 6.1 g (87%) as a dark red solid. ¹H NMR (300 MHz, CDCl₃) δ 7.81 (s, 1H), 6.94 (s, 1H), 2.45 (m, 1H), 1.26-1.46 (m, 40H), 0.87 (t, 6H).

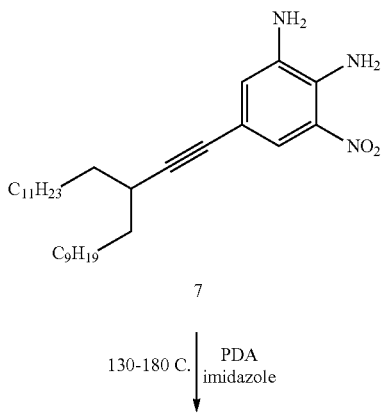

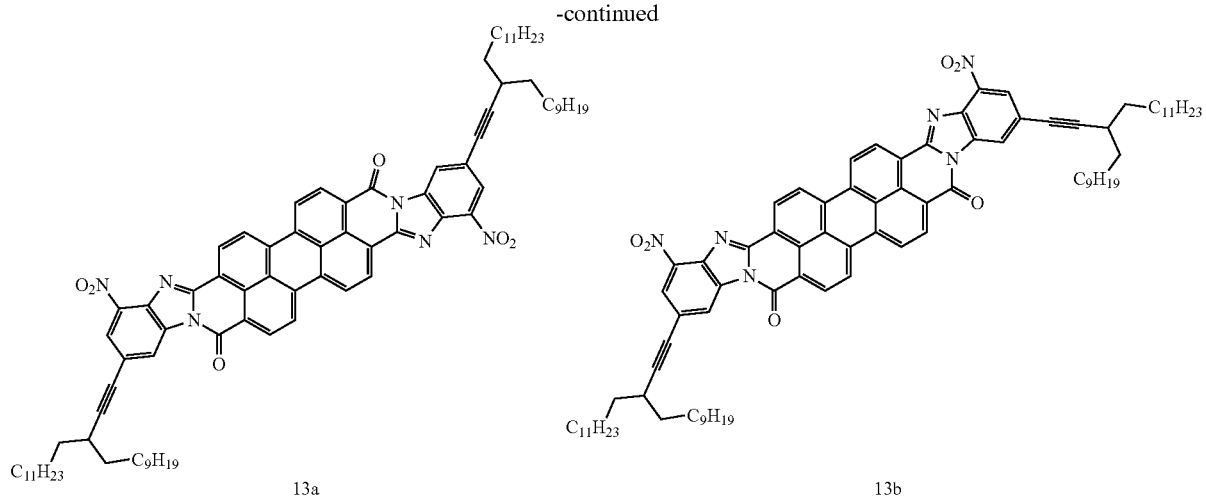

13a 13b

To a 25 mL flask was added compound 7 (5.10 g, 10.2 mmol, 2.2 eq), PDA (1.70 g, 4.60 mmol, 1 eq.) and Imidazole (21.0 g, 325 mmol, 70 eq). The mixture was degassed under vacuum and purged with $N_2$ three times. The reaction was stirred at 130° C. for 3 h and 180° C. for 12 h. The dark purple mixture was cooled down. The solid was washed with water (3×2 mL) and EtOH (3×2 mL), vacuum dried to give products 13a and 13b 6.2 g (100%) as a dark purple solid.

Example 8

This example describes synthesis of the disclosed organic compound wherein Core is PANI type (electro-conductive oligomer structure 22 from Table 2) according following structural schemes:

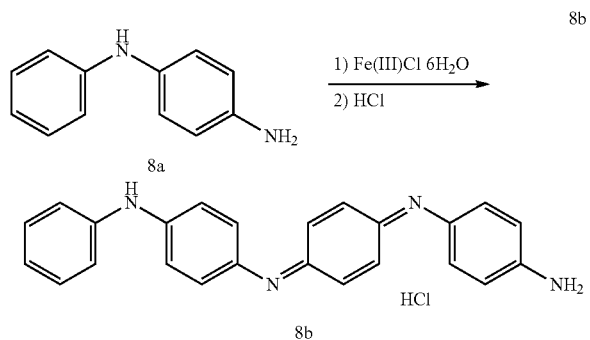

8a

8b

A 5 L 3-neck flask equipped with a magnetic stirrer and addition funnel was charged with Nphenyl-1,4-benzenediamine (328.5 mmol, 60.5 g) then 1M HCl (2 L). Let stir 20 min. Added an additional 200 mL 1M HCl to get all starting material into solution. $FeCl_3$ $H_2O$ (328.5 mmol, 88.8 g) was dissolved in 1M HCl (500 mL) and transferred to the addition funnel. The iron solution was added over 5 minutes to the starting amine solution. The sludgy solution was diluted with additional water (500 mL). Reaction was stirred vigorously for 4 hours. Using a giant Buchner funnel the reaction mixture was filtered (5-7 hours total for complete filtration). The filter cake was washed with water until pH was neutral and then continued washing (3 L total). The brilliant blue green solid was triturated with acetone/water/ 1M HCl (5:2:5) in a 2 L round bottom flask equipped with a mechanical stirrer. The suspension was stirred vigorously for 4 hours. The suspension was filtered, the filter cake washed with water (2 L), giving a blue green solid (46.7 g, 71% yield).

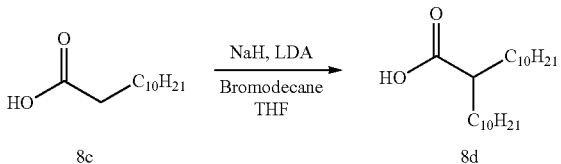

8c 8d

A clean dry 2 L 3-neck flask equipped with a mechanical stirrer and Ar inlet/outlet was charged with dodecanoic acid 8c (149.8 mmol, 30.0 g). Anhydrous tetrahydrofuran (THF) (1 L) was cannulated into the flask and the solution was sparged with Ar. The reaction mixture was then cooled to 0° C. Powdered NaH (164.8 mmol, 3.96 g) was added in two equivalent portions (30 minutes between additions). Breaking from normal experimental speak, this part of the reaction is extremely touchy. At 0° C., there is no evolution of hydrogen gas, but if the solutions gets above approx. 10° C. there is massive evolution of hydrogen gas. To counter this, remove the ice bath until gas evolution started and then put it back in the ice bath once the internal temperature reached about 5-8° C. (cycled through ice bath/no ice bath until all gas evolution ceased when the internal temperature is in the range of 10-15° C. or greater. In tandem, a separate clean dry 500 mL round bottom flask was charged with anhydrous THF (100 mL) and diisopropyl amine (180 mmol, 18.2 g). The resulting solution was cooled in an ice/methanol (MeOH) bath. N-Butyllithium solution (2.36 M in hexanes determined by titration, 180 mmol, 76.3 mL) was cannulated into the diisopropyl amine solution and lithium diisopropylamide (LDA) was formed by allowing the reagents to react for 30 minutes. Once gas evolution of the decanoic acid solution had ceased the formed LDA solution was cannulated into it in 5-10 mL portions (total time 45 minutes). After addition was complete, the reaction was allowed to stir at 0° C. for 10 minutes, at which time the ice bath was removed with additional stirring for 30 minutes. Bromodecane (164.8 mmol, 41.0 g) was added in one portion. The flask was then placed in an oil bath and heated to 45° C. (external temp.). The reaction was allowed to stir, with heating, for 16 hours. The reaction mixture was carefully quenched with water (50 mL) and then acidified with 1M HCl (300 mL) to pH=2. The layers were separated and the aqueous layer was extracted with THF (2×500 mL). The combined organics were washed with brine (1×500 mL), dried (Na$_2$SO$_4$), filtered and concentrated in vacuo. The resultant sludgy solid was stirred with hexanes (300 mL) for 1 hour, filtered over diatomaceous silica and the mother liquor was stripped. The resultant solid was cold triturated with ethanol (EtOH) (200 mL) in a −10° C. MeOH/ice bath, letting stir for 30 minutes. The suspension was filtered, washing with ice cold EtOH and the filter cake was dried under vacuum until constant weight. The title compound 8d (32.4 g, 64%) was isolated as a white powder. NMR (CDCl3) d 2.33 (q, 1H), 1.2-1.5 (m, 4H) 1.15 (m, 32H) 0.84 (t, 6H).

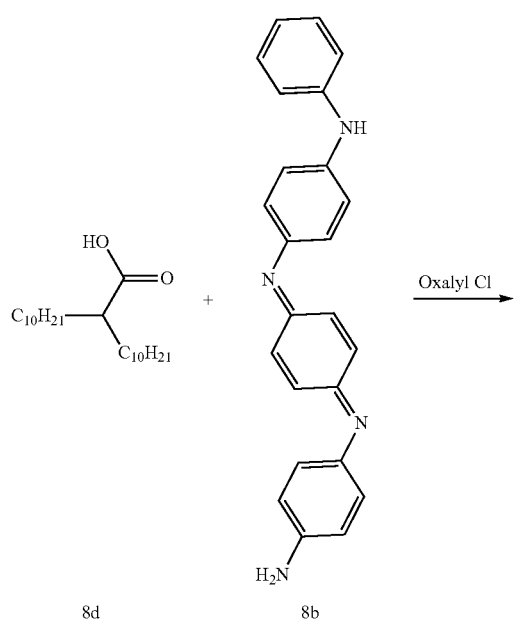

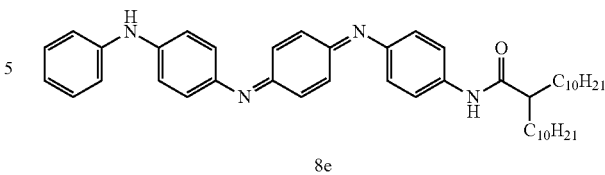

A clean dry 1 L 3-neck flask equipped with a stir bar, addition funnel and Ar inlet was charged with 2-decyldodecanoic acid 8d (26.0 g, 76.3 mmol) and dichloromethane (300 mL). The addition funnel was charged with dichloromethane (40 mL) and oxalyl chloride (2M in dichloromethane, 42 mL, 84.0 mmol). The oxalyl chloride solution was added dropwise over 1H and the reaction mixture was stirred at room temperature overnight. The solvent was removed under reduced pressure and the resulting acid chloride was dried under vacuum until at constant weight. Under the assumption that there was 100% conversion to the acid chloride the yellow oil was dissolved in dichloromethane to give a 0.3M solution. A separate clean dry 1 L 3-neck flask equipped with a stir bar, addition funnel and Ar inlet was charged with pyridine (300 mL), molecular sieves and 8b HCl (9.42 g, 23.5 mmol). To the addition funnel was added 78.3 mL of the 0.3M acid chloride solution. The acid chloride was added dropwise over 3 hours and the reaction was allowed to stir overnight at room temperature. The molecular sieves were removed via filtration over a short pad of diatomaceous silica and the mother liquor was diluted with THF (300 mL). The organic layer was washed with brine (5×100 mL), dried (Na$_2$SO$_4$), filtered over diatomaceous silica and concentrated in vacuo. The resulting solid was triturated with toluene/MeOH (1 L, 7:3), stirring overnight. The ppt was filtered away and the mother liquor was concentrated in vacuo to afford 8e (15.65 g, 97%) as a dark purple/blue solid.

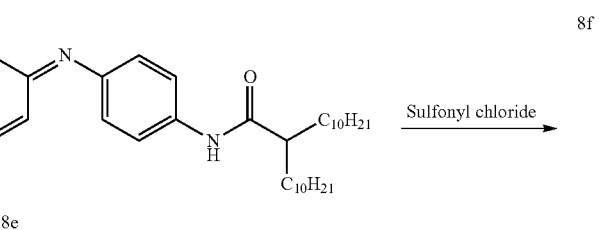

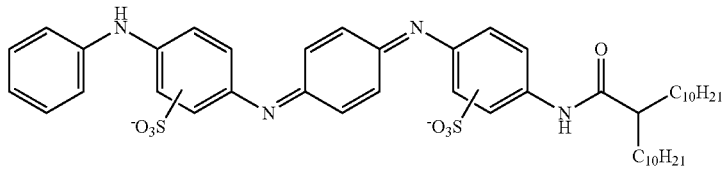

A clean dry 1 L 3-neck flask equipped with an addition funnel and reflux condenser was charged with 8e (14.4 g, 21 mmol) and dichloroethane (400 mL). The suspension was heated in an oil bath and the addition funnel was charged with sulfonyl chloride (4.89 g, 42 mmol) and dichloroethane (40 mL). Once the reaction mixture was at reflux, addition of the sulfonyl chloride solution began (time of addition=1H). The reaction was allowed to reflux for an additional hour once addition was complete. The reaction mixture was cooled to room temperature and the resulting sludgy suspension was filtered over filter paper. The filter cake was washed with dichloroethane (200 mL) and then hexanes (200 mL). Crude 8f was allowed to dry on the funnel overnight. The solid was suspended in water (500 mL) and refluxed for 5 hours. The suspension was cooled to and the solvent was reduced to 80% of its original volume. The product was precipitated with acetone and the suspension stirred overnight. The solid was filtered away and the filter cake was washed with acetone (200 mL) and dried in a vacuum desiccator for 48 hours. The mother liquor was concentrated to dryness by co-evaporation with acetone. The resulting solid was triturated with acetone (200 mL), filtered and dried in a vacuum desiccator for 48 hours. The solids were combined to afford 8f (11.2 g, 63% yield)

Example 9

This example describes synthesis of the disclosed organic compound wherein Core is PANI type (electro-conductive oligomer structure 22 from in Table 2) according following synthetic scheme:

A 3 L round bottom flask was charged with 4,4'-diaminodiphenyl amine sulfate hydrate (50.0 g), 100° C. 1% (w/w) KOHaq (2 L) and $Na_2S_2O_5$ (24 g). The mixture was allowed to stir for 15 minutes and then cooled to 40° C. in an ice bath. The precipitate was collected via filtration and the filter cake was rinsed with water. The collected solid 9a was dried in a vacuum desiccator for 72 hours. A clean dry 500 mL round bottom flask equipped with an Ar inlet and stir bar was charged with diamine 9a (24.5 g, 82.4 mmol), 4-fluoronitrobenzene 9b (23.3 g, 164.8 mmol), triethylamine (Et3N) (20.8 g, 101.2 mmol) and dimethyl sulfoxide (DMSO) (250 mL). The reaction was heated in a 90° C. oil bath for 72 hours. The reaction mixture was cooled to room temperature and the crude product was precipitated by adding water (2 L). The precipitate was collected by filtration, rinsed with hexanes (500 mL) and dried in a vacuum desiccator for 24 hours. The crude dinitro was triturated with $CHCl_3$ (500 mL), with vigorous stirring to break up the material, and collected by filtration, rinsing with $CHCl_3$ and dried in a vacuum desiccator overnight. The crude material was then triturated with tetrahydrofuran (THF)/$CH_2Cl_2$ (500 mL), collected by filtration and dried in a vacuum desiccator for 24 hours to afford $N^1$-(4-nitrophenyl)-$N^4$-[4-[(4-nitrophenyl)amino]phenyl]-1,4-Benzenediamine (32.9 g, 90%) as a rust colored solid. A 2 L Parr hydrogenation flask was charged with Pd/C (400 mg), ethanol (EtOH)/THF (1:1, 1 L) and $N^1$-(4-nitrophenyl)-$N^4$-[4-[(4-nitrophenyl)amino]phenyl]-1,4-Benzenediamine (32.0 g, 72.5 mmol). The flask was evacuated via vacuum and charged with $H_2$ three times and hydrogenated in a Parr shaker for 48 hours. The reaction mixture was evacuated via vacuum to remove hydrogen and back flushed with $N_2$ three times. The solution was allowed to sit under ambient conditions overnight. The Pd/C was filtered away over diatomaceous silica rinsing with methanol (MeOH) (200 mL) and acetone (200 mL) and the mother liquor was concentrated in vacuo. The resulting solid was triturated with 1M HCl (500 mL), stirring overnight. The suspension was filtered over No. 54 filter paper, rinsing with water (500 mL). The filter cake was then deprotonated by suspending in 2M $NH_4OH$ and stirring vigorously. The aqueous layer was extracted with THF (1×300 mL), ethyl acetate (EtOAc) (1×300 mL). The combined organics were washed with brine (1×500 mL) and concentrated in vacuo and then dried in a vacuum desiccator for 48 hours to afford the title compound 9c (10.1 g, 37%) as a dark purple/blue solid.

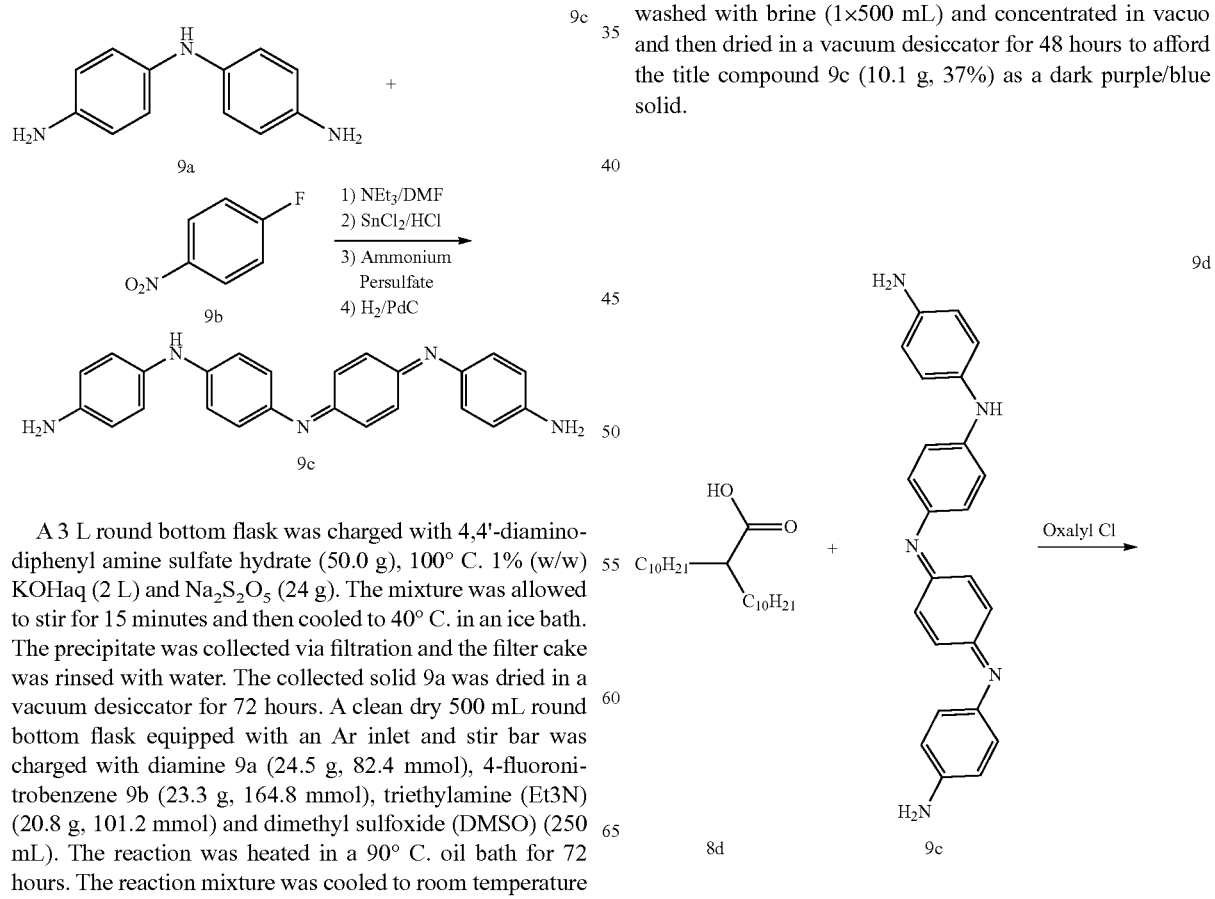

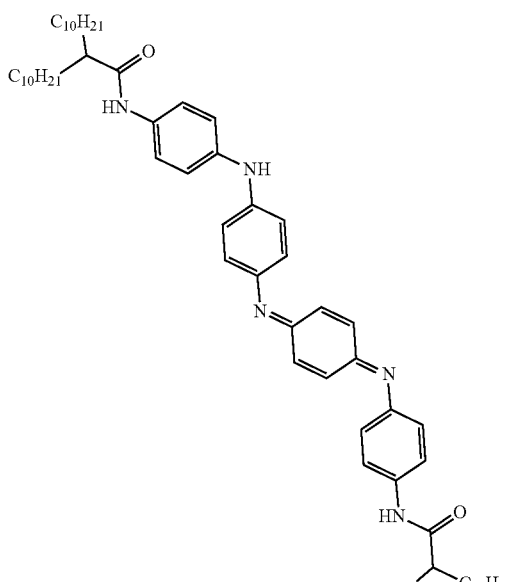

9d

A clean dry 1 L 3-neck flask equipped with a stir bar, addition funnel and Ar inlet was charged with 2-decyldodecanoic acid 8d (18.0 g, 52.8 mmol) and dichloromethane (200 mL). The addition funnel was charged with dichloromethane (40 mL) and oxalyl chloride (2M in dichloromethane, 29 mL, 58.1 mmol). The oxalyl chloride solution was added dropwise over 1 hour and the reaction mixture was stirred at room temperature overnight. The solvent was removed under reduced pressure and the resulting acid chloride was dried under vacuum until at constant weight. Under the assumption that there was 100% conversion to the acid chloride the yellow oil was dissolved in dichloromethane to give a 0.3M solution. A clean dry 1 L round bottom flask equipped with a stir bar, addition funnel and Ar inlet was charged compound 9c (10.0 g, 26.4 mmol) molecular sieves (20 g) and pyridine (400 mL). The addition funnel was charged with $CH_2Cl_2$ (100 mL) and the acid chloride (173 mL, 0.3M in $CH_2Cl_2$, 52.8 mmol). The acid chloride was added dropwise over 4 hours. The reaction was stirred at room temperature overnight. The reaction was filtered over diatomaceous silica to remove the molecular sieves and the diatomaceous silica was then rinsed with THF (300 mL). The mother liquor was transferred to a separatory funnel and the organic layer was washed repeatedly with brine (4.5 L total), dried ($Na_2SO_4$), filtered over diatomaceous silica and concentrated (pyridine was removed by azeotropic distillation with heptane 4×300-400 mL). The crude material was then dried in a vacuum desiccator for 4 hours. The resulting solid was triturated with hexanes (500 mL) and put in a −25° C. freezer for 48 hours. The suspended solid was recovered by filtration, rinsing the filter cake with ice cold hexanes (100 mL). The filter cake was then dried to constant weight in a vacuum desiccator to afford the title compound 9d (9.9 g). The mother liquor was concentrated in vacuo suspended in Et20 and concentrated 3 times. The resultant solid was triturated with toluene (250 mL), filtered and dried in a vacuum desiccator to afford additional 9d (12.5 g, 22.4 g total, 83% yield) as a purple blue solid.

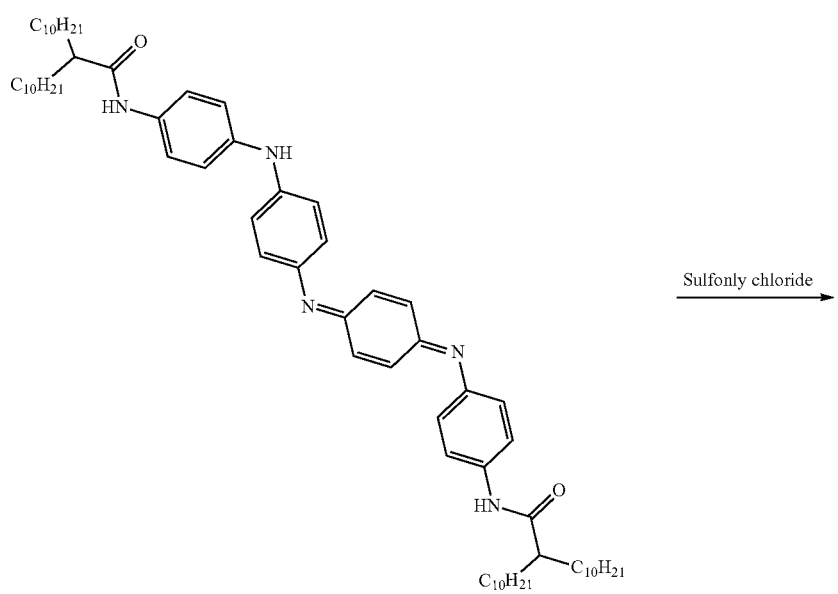

9d

-continued

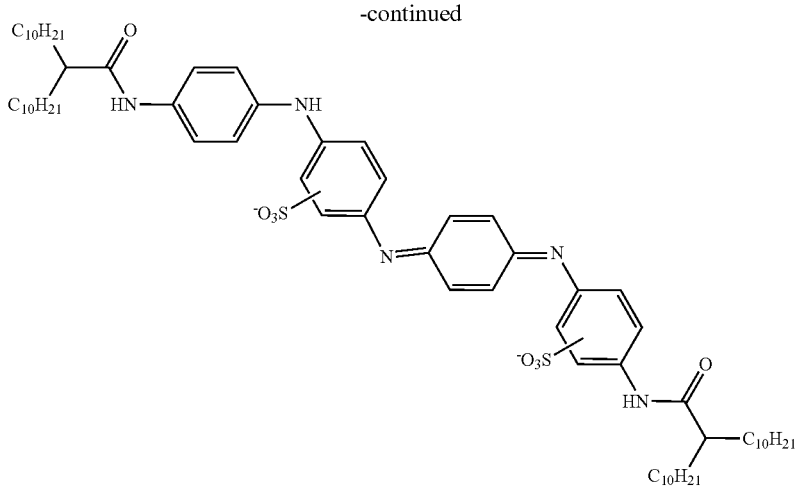

9e

A clean dry 3-neck flask equipped with a stir bar, reflux condenser and addition funnel was charged with 9d (11.6 g, 11.3 mmol) and dichloroethane (300 mL). The addition funnel was charged with dichloromethane (30 mL) and sulfonyl chloride (2.63 g, 22.6 mmol). The reaction was heated to reflux in an oil bath. Once at reflux the sulfonyl chloride solution was added dropwise over 1.5 hours. Once addition complete the reaction was stirred at reflux for an additional 2 hours. The reaction was cooled and then the solvent was removed under reduced pressure. The resulting solid was suspended in water (500 mL) and heated to reflux overnight. Upon cooling the solid was isolated by filtration and dried in a vacuum desiccator for 24 hours affording 9e (12.1 g, 88%) as a dark purple/blue solid.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature described herein, whether preferred or not, may be combined with any other feature described herein, whether preferred or not. In the claims that follow, the indefinite article "A", or "An" refers to a quantity of one or more of the item following the article, except where expressly stated otherwise. As used herein, in a listing of elements in the alternative, the word "or" is used in the logical inclusive sense, e.g., "X or Y" covers X alone, Y alone, or both X and Y together, except where expressly stated otherwise. Two or more elements listed as alternatives may be combined together. The appended claims are not to be interpreted as including means-plus-function limitations, unless such a limitation is explicitly recited in a given claim using the phrase "means for."

What is claimed is:

1. An organic compound characterized by electronic polarizability and having a general structural formula selected from:

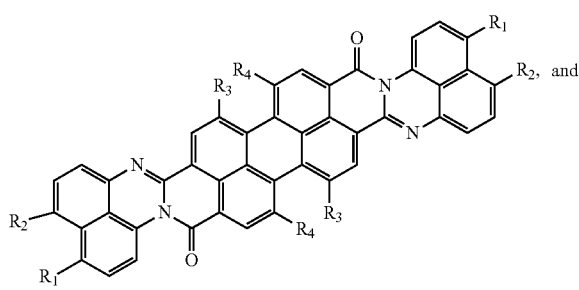
24

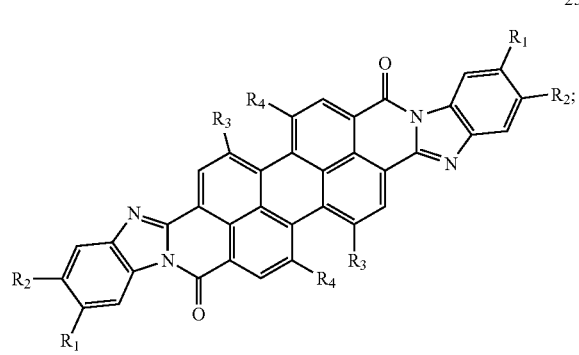
25 wherein:

$R_1$ is independently selected from the group consisting of hetero-alkyl $C_1$-$C_{18}$, hetero-alkenyl $C_1$-$C_{18}$, hetero-alkynyl $C_1$-$C_{18}$, hetero-aryl $C_1$-$C_{18}$, unsubstituted $C_1$-$C_{18}$ alkyl, substituted $C_1$-$C_{18}$ alkyl, unsubstituted $C_2$-$C_{18}$ alkenyl, substituted $C_2$-$C_{18}$ alkenyl, unsubstituted $C_2$-$C_{18}$ alkynyl, substituted $C_2$-$C_{18}$ alkynyl, unsubstituted $C_4$-$C_{18}$ aryl, substituted $C_4$-$C_{18}$ aryl, fluorinated alkyl, chlorinated alkyl, branched alkyl, branched fluorinated alkyl, and branched chlorinated alkyl;

wherein the core has flat anisometric form and $R_2$ are selected from hydrogen and nucleophilic groups and $R_3$ and $R_4$ are independently selected from hydrogen and electrophilic groups or vice versa $R_3$ and $R_4$ are independently selected from hydrogen and nucleophilic groups.

2. The organic compound according to claim 1, wherein the Core is centrosymmetric.

3. The organic compound according to claim 1, wherein the Core is non-centrosymmetric.

4. The organic compound according to claim 1, wherein the electrophilic groups are selected from —$NO_2$, —$NH_3^+$ and —$NR_3^+$ and —$NRR'R''^+$ (with counterion —$Cl^-$ or —$Br^-$), —CHO, —CRO, —$SO_3H$, —$SO_3R$, —$SO_2NH_2$, —$SO_2NRR'$, —COOH, —COOR, —COCl, —$CONH_2$, —CONRR', —$CF_3$, —$CCl_3$, —CN, wherein R and R' and R" are radicals independently selected from the list comprising alkyl, allyl, benzyl groups, phenyl and other aryl groups.

5. The organic compound according to claim 1, wherein the nucleophilic groups are selected from —$O^-$, —$NH_2$, —NHR, —$NR_2$, —OH, —OR, —NHCOR, —OCOR, alkyls, —$C_6H_5$, vinyls, wherein R is radical selected from the list comprising alkyl, allyl benzyl groups, phenyl and other aryl groups.

6. A dielectric layer comprising the organic compound according to claim 1.

7. The dielectric layer according to claim 6, wherein the dielectric layer is crystalline.

8. A capacitor comprising a first electrode, a second electrode, and a dielectric layer according to claim 6 is disposed between said first and second electrodes, wherein said electrodes are more or less flat and planar and positioned more or less parallel to each other.

\* \* \* \* \*